(12) United States Patent
Desbordes et al.

(10) Patent No.: US 9,102,588 B2
(45) Date of Patent: Aug. 11, 2015

(54) FUNGICIDE N-CYCLOALKYL-N-BICYCLIC-CARBOXAMIDE DERIVATIVES

(71) Applicants: Philippe Desbordes, Lyons (FR); Stephanie Gary, Champagne au Mont d'Or (FR); Marie-Claire Grosjean-Cournoyer, Curis au Mont d'Or (FR); Benoit Hartmann, Sainte Foy les Lyon (FR); Hiroyuki Hadano, Shimotsuke (JP); Philippe Rinolfi, Chatillon D'azergues (FR); Jean-Pierre Vors, Sainte Foy les Lyon (FR)

(72) Inventors: Philippe Desbordes, Lyons (FR); Stephanie Gary, Champagne au Mont d'Or (FR); Marie-Claire Grosjean-Cournoyer, Curis au Mont d'Or (FR); Benoit Hartmann, Sainte Foy les Lyon (FR); Hiroyuki Hadano, Shimotsuke (JP); Philippe Rinolfi, Chatillon D'azergues (FR); Jean-Pierre Vors, Sainte Foy les Lyon (FR)

( * ) Notice: Subject to any disclaimer, the term of this patent is extended or adjusted under 35 U.S.C. 154(b) by 0 days.

(21) Appl. No.: 13/683,218

(22) Filed: Nov. 21, 2012

(65) Prior Publication Data

US 2013/0079524 A1 Mar. 28, 2013

Related U.S. Application Data

(62) Division of application No. 12/452,887, filed as application No. PCT/EP2008/060037 on Jul. 31, 2008, now Pat. No. 8,334,390.

(30) Foreign Application Priority Data

Jul. 31, 2007 (EP) .................................. 07356103
Apr. 16, 2008 (EP) .................................. 08356060

(51) Int. Cl.

| | | |
|---|---|---|
| *C07D 513/02* | (2006.01) | |
| *C07C 217/74* | (2006.01) | |
| *C07D 231/16* | (2006.01) | |
| *C07D 307/68* | (2006.01) | |
| *C07D 405/12* | (2006.01) | |
| *C07D 409/12* | (2006.01) | |
| *C07D 411/12* | (2006.01) | |
| *C07C 211/42* | (2006.01) | |
| *C07D 215/40* | (2006.01) | |
| *C07D 311/68* | (2006.01) | |
| *C07D 335/06* | (2006.01) | |

(52) U.S. Cl.
CPC ............. *C07C 217/74* (2013.01); *C07C 211/42* (2013.01); *C07D 215/40* (2013.01); *C07D 231/16* (2013.01); *C07D 307/68* (2013.01); *C07D 311/68* (2013.01); *C07D 335/06* (2013.01); *C07D 405/12* (2013.01); *C07D 409/12* (2013.01); *C07D 411/12* (2013.01)

(58) Field of Classification Search
None
See application file for complete search history.

(56) References Cited

U.S. PATENT DOCUMENTS

| | | | |
|---|---|---|---|
| 3,511,842 A | 5/1970 | Sallman | 260/288 |
| 3,513,244 A | 5/1970 | Gittos et al. | 424/320 |
| 3,534,055 A | 10/1970 | Gittos et al. | 260/295 |
| 3,657,258 A * | 4/1972 | Treiber | 546/206 |
| 5,330,995 A | 7/1994 | Eicken et al. | 514/355 |

FOREIGN PATENT DOCUMENTS

| | | |
|---|---|---|
| CN | 1708487 A | 12/2005 |
| DE | 1793590 A1 | 2/1972 |
| EP | 0545099 A2 | 6/1993 |
| GB | 1037014 | 7/1966 |
| GB | 1120700 | 7/1968 |
| GB | 1187017 | 4/1970 |
| JP | 63-201178 | 8/1988 |
| JP | 2-131481 | 5/1990 |
| JP | 2001-316366 | 11/2001 |
| JP | 2008-510006 | 4/2008 |
| WO | WO 93/11117 | 10/1993 |
| WO | WO 01/55124 | 8/2001 |
| WO | WO 02/32856 | 4/2002 |
| WO | WO 2004/039789 | 5/2004 |

(Continued)

OTHER PUBLICATIONS

CAPLUS 1981:454631.*

(Continued)

*Primary Examiner* — Heidi Reese
(74) *Attorney, Agent, or Firm* — Ostrolenk Faber LLP

(57) ABSTRACT

The present invention relates N-cycloalkyl-N-bicyclic-carboxamide, thiocarboxamide or N-substituted carboximidamide derivatives of formula (I) wherein A represents a carbolinked, 5-membered heterocyclyl group; T represents O, S, N—$R^a$, N—$OR^a$, N—$NR^aR^b$ or N—CN; $Z^1$ represents a $C_3$-$C_7$-cycloalkyl group; X represents N or a $CZ^7$ and $Z^2$; $Z^3$; $L^1$ and $L^2$ represent various substituents; their process of preparation; preparation intermediate compounds; their use as fungicide active agents, particularly in the form of fungicide compositions and methods for the control of phytopathogenic fungi, notably of plants, using these compounds or compositions.

(I)

5 Claims, No Drawings

(56) References Cited

FOREIGN PATENT DOCUMENTS

WO    WO 2006023400 A2 *   3/2006
WO    WO 2007/014290      2/2007

OTHER PUBLICATIONS

International Search Report dated Mar. 3, 2009, issued in corresponding International Application No. PCT/EP2008/060037.

Database CHEMCATS, Chemical Abstracts Service, Columbus, Ohio, US; XP002462025, Order Nos. (ON): AKE-BBV-015557, AKE-BBV-014916, BBV-015557 and BBV-014916, abstract.

Patent family search for DE1793590 (equiv. GB 1,037,014), 1/5/1 Dialog(R) File 351:Derwent abstract, 0000115017, WPI Acc No. 1966-15719F/196800, "N-substd 1-aminoindane derivs", http://wvvw.dialogclassic.com/MainFrame.jsp Jan. 26, 2010.

Douglas B. Grotjahn, Synthesis and Characterization of 5H-1,3-Dioxolo[4,5-*f*]indoleethylamines, J. Heterocyclic Chem., 20, pp. 1031-1036 (1983).

K.C. Nicolaou et al., "o-Iodoxybenzoic Acid (IBX) as a Viable Reagent in the Manipulation of Nitrogen-and Sulfur-Containing Substrates: Scope, Generality, and Mechanism of IBX-Mediated Amine Oxidations and Dithiane Deprotections", J. Am. Chem. Soc., 126, pp. 5192-5201 (2004).

Krisztina Vukics et al. "Synthesis of C-Aryl-N-cyclopropylnitrones", Synthetic Communications, vol. 33, No. 19, pp. 3419-3425 (2003).

Masatoshi Yamato et al., "Reactivity of Isocoumarins. III.[1)] Reaction of 1-Ethoxyisochroman with Benzylamines", Chem. Pharm. Bull, 29(3) pp. 720-725, (1981).

R. Sustmann et al., "Methoden der organischen Chemie", Houben-Weyl, vol. E5/1, pp. 628-633 (1985). English translation attached.

Jean-Albert Gautier, et al., "Preparation and synthetic uses of amidines", Chapter 7, pp. 296-301, *The Chemistry of the Functional Groups* (Editor: S. Patai), Wiley, New York, (1975).

B. Cottineau et al. "Synthesis and Hypoglycemic Evaluation of Substituted Pyrazole-4-carboxylic Acids", Bioorganic & Medicinal Chemistry Letters 12 (2002) pp. 2105-2108.

L.T. Belen'kii et al., "Reductive Condensation of Trichloromethylarenes with Hydroxylamine and Hydrazines in Pyridine", Tetrahedron, vol. 47, No. 3, pp. 447-456 (1991).

Steven V. Ley et al. "A polymer-supported thionating reagent", J. Chem. Soc., Perkin Trans. 1, (2001) pp. 358-361.

U.S. Appl. No. 12/452,893, filed Jan. 26, 2010 by Philippe Desbordes et al. entitled "Fungicide 2 Pyridyl-Methylene-Thio Carboxamide or 2-Pyridyl-Methylene-N-Substituted Carboximidamide Derivatives".

U.S. Appl. No. 12/452,910, filed Jan. 27, 2010 by Philippe Desbordes et al. entitled "Fungicide N-5-Membered Fused Heteroaryl-Methylene-N-Cycloalkyl-Carboxamide Derivatives".

U.S. Appl. No. 12/452,925, filed Jan. 28 2010 by Philippe Desbordes et al. entitled "Fungicidal N-Cycloalkyl-Benzyl-Thiocarboxamides or N-Cycloalkyl-Benzyl-N'-Substituted-Amidine Derivatives".

U.S. Appl. No. 12/452,921, filed Jan. 28, 2010 by Philippe Desbordes et al. entitled Fungicide N-6-Membered Fused (Hetero) Aryl-Methylenen-Cycloalkyl Carboxamide Derivatives.

* cited by examiner

FUNGICIDE N-CYCLOALKYL-N-BICYCLIC-CARBOXAMIDE DERIVATIVES

This application is a divisional application of Ser. No. 12/452,887 filed on Mar. 29, 2010, which is a 35 U.S.C. §371 national phase conversion of PCT/EP2008/060037, filed on Jul. 31, 2008, which claims priority to European Application No. 07356103.7, filed on Jul. 31, 2007 and European Application No. 08356060.7, filed on Apr. 16, 2008, the entire contents of which are hereby incorporated by reference.

The present invention relates to N-cycloalkyl-N-bicyclic-carboxamide, thiocarboxamide or N-substituted carboximidamide derivatives, their process of preparation, preparation intermediate compounds, their use as fungicide active agents, particularly in the form of fungicide compositions, and methods for the control of phytopathogenic fungi, notably of plants, using these compounds or compositions.

In international patent application WO-2007/014290 certain N-substituted-N-bicyclic-carboxamide or thiocarboxamide derivatives are generically embraced in a broad disclosure of numerous compounds of the following formula:

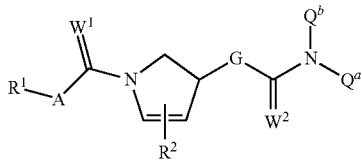

wherein $W^1$ can represent oxygen or sulphur; A can represent NH or $CH_2$; $R^1$ can represent a phenyl or heterocyclic ring; G can represent a 5-membered heterocyclic ring, more specifically a thiazole ring; $W^2$ can represent oxygen or sulphur; $Q^a$ can represent $C_4$-$C_7$-cycloalkyl and $Q^b$ can represent a 8-11-membered, partially saturated, bicyclic system. However, this document does not specifically disclose nor suggest to select such compounds wherein the nitrogen atom of the $N$-$Q^a Q^b$ moiety can be substituted by a cycloalkyl.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds that possess the above mentioned effects or advantages.

Accordingly, the present invention provides N-cycloalkyl-N-bicyclic-carboxamide derivatives of formula (I)

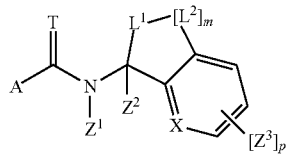

wherein
A represents a carbo-linked, partially saturated or unsaturated, 5-membered heterocyclyl group that can be substituted by up to four groups R;

T represents O, S, N—$R^a$, N—$OR^a$, N—$NR^a R^b$ or N—CN;

$Z^1$ represents a non substituted $C_3$-$C_7$-cycloalkyl or a $C_3$-$C_7$ cycloalkyl substituted by up to 10 atoms or groups that can be the same or different and that can be selected in the list consisting of halogen atoms; cyano; $C_1$-$C_8$-alkyl; $C_1$-$C_8$-halogenoalkyl comprising up to 9 halogen atoms that can be the same or different; $C_1$-$C_8$-alkoxy; $C_1$-$C_8$-halogenoalkoxy comprising up to 9 halogen atoms that can be the same or different; $C_1$-$C_8$-alkoxycarbonyl; $C_1$-$C_8$-halogenoalkoxycarbonyl comprising up to 9 halogen atoms that can be the same or different; $C_1$-$C_8$-alkylaminocarbonyl; di-$C_1$-$C_8$-alkylaminocarbonyl or carbamoyl;

$Z^2$ represents a hydrogen atom; a halogen atom; cyano; $C_1$-$C_8$-alkyl; $C_1$-$C_8$-halogenoalkyl comprising up to 9 halogen atoms that can be the same or different;

$L^1$ and $L^2$, that can be the same or different, represent $CZ^4 Z^5$, $NZ^6$, O, S, S(O) or $S(O)_2$;

m represents 1, 2 or 3;

X represents $CZ^7$ or N;

$Z^3$ and $Z^7$, that can be the same or different, represent a hydrogen atom; a halogen atom; nitro; cyano; hydroxyl; thio; amino; pentafluoro-λ6-thio; $C_1$-$C_8$-alkyl; $C_1$-$C_8$-halogenoalkyl comprising up to 9 halogen atoms that can be the same or different; $C_1$-$C_8$-alkylamino; di-$C_1$-$C_8$-alkylamino; $C_1$-$C_8$-alkoxy; $C_1$-$C_8$-halogenoalkoxy comprising up to 9 halogen atoms that can be the same or different; $C_1$-$C_8$-alkoxy-$C_1$-$C_8$-alkyl; $C_1$-$C_8$-alkylsulphanyl; $C_1$-$C_8$-halogenoalkylsulphanyl comprising up to 9 halogen atoms that can be the same or different; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different $C_2$-$C_8$-alkenyloxy; $C_2$-$C_8$-halogenoalkenyloxy comprising up to 9 halogen atoms that can be the same or different; $C_2$-$C_8$-alkynyloxy; $C_2$-$C_8$-halogenoalkynyloxy comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; formyloxy; formylamino; carboxy; carbamoyl; N-hydroxycarbamoyl; carbamate; (hydroxyimino)-$C_1$-$C_8$-alkyl; $C_1$-$C_8$-alkylcarbonyl; $C_1$-$C_8$-halogenoalkylcarbonyl comprising up to 9 halogen atoms that can be the same or different; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbarmoyl; N—$C_1$-$C_8$-alkyl-$C_1$-$C_8$-alkoxycarbarmoyl; $C_1$-$C_8$-alkoxycarbonyl; $C_1$-$C_8$-halogenoalkoxycarbonyl comprising up to 9 halogen atoms that can be the same or different; $C_1$-$C_8$-alkylaminocarbonyl; di-$C_1$-$C_8$-alkylaminocarbonyl; $C_1$-$C_8$-alkylcarbonyloxy; $C_1$-$C_8$-halogenoalkylcarbonyloxy comprising up to 9 halogen atoms that can be the same or different; $C_1$-$C_8$-alkylcarbonylamino; $C_1$-$C_8$-halogenoalkylcarbonylamino comprising up to 9 halogen atoms that can be the same or different; $C_1$-$C_8$-alkylaminocarbonyloxy; di-$C_1$-$C_8$-alkylaminocarbonyloxy; $C_1$-$C_8$-alkyloxycarbonyloxy, $C_1$-$C_8$-alkylsulphenyl, $C_1$-$C_8$-halogenoalkylsulphenyl comprising up to 9 halogen atoms that can be the same or different, $C_1$-$C_8$-alkylsulphinyl, $C_1$-$C_8$-halogenoalkylsulphinyl comprising up to 9 halogen atoms that can be the same or different, $C_1$-$C_8$-alkylsulphonyl, $C_1$-$C_8$-halogenoalkylsulphonyl comprising up to 9 halogen atoms that can be the same or different, $C_1$-$C_8$-alkoxyimino, ($C_1$-$C_8$- alkoxyimino)-$C_1$-$C_8$-alkyl, ($C_1$-$C_8$-alkenyloxyimino)-$C_1$-$C_8$-alkyl, ($C_1$-$C_8$-alkynyloxyimino)-$C_1$-$C_8$-alkyl, a (benzyloxyimino)-$C_1$-$C_8$-alkyl; tri($C_1$-$C_8$-alkyl)silyl; tri($C_1$-$C_8$-alkyl)silyl-$C_1$-$C_8$-alkyl; phenyl that can be substituted by up to 5 groups Q; benzyloxy that can be substituted by up to 5 groups Q; benzylthio that can be substituted by up to 5 groups Q; benzylamino that can be substituted by up to 5 groups Q; naphtyl that can be substituted by up to 6 groups Q; phenoxy that can be substituted by up to 5 groups Q; phenylamino that can be substituted by up to 5 groups Q; phenylthio that can be substituted by up to 5 groups Q; phenylmethylene that can be substituted by up to 5 groups Q; pyridinyl that can be substituted by up to four groups Q and pyridinyloxy that can be substituted by up to four groups Q; phenoxymethylene that can be substituted by up to 5 groups Q;

two substituents $Z^3$ or $Z^7$ together with the consecutive carbon atoms to that they are linked can form a 5- or 6-membered, saturated or non-saturated, carbo- or hetero-cycle, that can be substituted by up to four groups Q that can be the same or different;

p represents 1, 2, or 3;

R, that can be the same or different, represent hydrogen atom; halogen atom; cyano; nitro; amino; thio; pentafluoro-λ-6-thio; $C_1$-$C_8$-alkylamino; di-$C_1$-$C_8$-alkylamino; tri($C_1$-$C_8$-alkyl)silyl; $C_1$-$C_8$-alkylsulphanyl; $C_1$-$C_8$-halogenoalkylsulphanyl comprising up to 9 halogen atoms that can be the same or different; $C_1$-$C_8$-alkyl; $C_1$-$C_8$-halogenoalkyl comprising up to 9 halogen atoms that can be the same or different; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_1$-$C_8$-alkoxy; $C_1$-$C_8$-halogenoalkoxy comprising up to 9 halogen atoms that can be the same or different; $C_2$-$C_8$-alkenyloxy; $C_2$-$C_8$-alkynyloxy; $C_3$-$C_7$-cycloalkyl; $C_3$-$C_7$-cycloalkyl-$C_1$-$C_8$-alkyl; $C_1$-$C_8$-alkylsulphinyl; $C_1$-$C_8$-alkylsulphonyl; $C_1$-$C_8$alkoxyimino; ($C_1$-$C_8$-alkoxyimino)-$C_1$-$C_8$-alkyl; (benzyloxyimino)-$C_1$-$C_8$-alkyl; phenoxy; benzyloxy; benzylthio; benzylamino; naphtyl; halogenophenoxy comprising up to 9 halogen atoms that can be the same or different; $C_1$-$C_8$-alkylcarbonyl; $C_1$-$C_8$-halogenoalkylcarbonyl comprising up to 9 halogen atoms that can be the same or different; $C_1$-$C_8$-alkoxycarbonyl; $C_1$-$C_8$-halogenoalkoxycarbonyl comprising up to 9 halogen atoms that can be the same or different; $C_1$-$C_8$-alkylaminocarbonyl; di-$C_1$-$C_8$-alkylaminocarbonyl;

$R^a$ and $R^b$, that can be the same or different, represent a hydrogen atom; $C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; $C_1$-$C_8$-alkylcarbonyl; $C_1$-$C_8$-halogenoalkylcarbonyl comprising up to 9 halogen atoms that can be the same or different; $C_1$-$C_8$-alkylsulphonyl; $C_1$-$C_8$-halogenoalkylsulphonyl comprising up to 9 halogen atoms that can be the same or different; phenyl that can be substituted by up to 5 groups Q; naphthyl that can be substituted by up to 6 groups Q; phenylmethylene that can be substituted by up to 5 groups Q; phenylsulphonyl that can be substituted by up to 5 groups Q;

$Z^4$ and $Z^5$, that can be the same or different, represent a hydrogen atom; a halogen atoms; cyano; nitro, $C_1$-$C_8$-alkyl; $C_1$-$C_8$-halogenoalkyl comprising up to 9 halogen atoms that can be the same or different; $C_1$-$C_8$-alkoxy; $C_1$-$C_8$-halogenoalkoxy comprising up to 9 halogen atoms that can be the same or different; $C_1$-$C_8$-alkoxy-$C_1$-$C_8$-alkyl; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; $C_1$-$C_8$-alkylcarbonyl; $C_1$-$C_8$-halogenoalkylcarbonyl comprising up to 9 halogen atoms that can be the same or different; $C_1$-$C_8$-alkylsulphanyl; $C_1$-$C_8$-halogenoalkylsulphanyl comprising up to 9 halogen atoms that can be the same or different; $C_1$-$C_8$-alkylsulphinyl; $C_1$-$C_8$-halogenoalkylsulphinyl comprising up to 9 halogen atoms that can be the same or different; $C_1$-$C_8$-alkylsulphonyl; $C_1$-$C_8$-halogenoalkylsulphonyl comprising up to 9 halogen atoms that can be the same or different;

$Z^6$ represents a hydrogen atom; $C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl, $C_1$-$C_8$-alkylcarbonyl; $C_1$-$C_8$-halogenoalkylcarbonyl comprising up to 9 halogen atoms that can be the same or different; $C_1$-$C_8$-alkylsulphonyl; $C_1$-$C_8$-halogenoalkylsulphonyl comprising up to 9 halogen atoms that can be the same or different; phenylsulfonyl can be substituted by up to 5 groups Q; benzyl that can be substituted by up to 5 groups Q;

Q, that can be the same or different, represents a halogen atom; cyano; nitro; $C_1$-$C_8$-alkyl; $C_1$-$C_8$-halogenoalkyl comprising up to 9 halogen atoms that can be the same or different; $C_1$-$C_8$-alkoxy; $C_1$-$C_8$-halogenoalkoxy comprising up to 9 halogen atoms that can be the same or different; $C_1$-$C_8$-alkylsulphanyl; $C_1$-$C_8$-halogenoalkylsulphanyl comprising up to 9 halogen atoms that can be the same or different; tri($C_1$-$C_8$)alkylsilyl and tri($C_1$-$C_8$)alkylsilyl-$C_1$-$C_8$-alkyl;

as well as salts, N-oxides, metallic complexes, metalloidic complexes and optically active or geometric isomers thereof.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods that are known per se by the man ordinary skilled in the art.

According to the invention, the following generic terms are generally used with the following meanings:

halogen means fluorine, chlorine, bromine or iodine;

heteroatom can be nitrogen, oxygen or sulphur;

halogenated groups, notably haloalkyl, haloalkoxy and cycloalkyl groups, can comprise up to nine identical or different a halogen atoms;

Any alkyl, alkenyl or alkynyl group can be linear or branched;

the term "aryl" means phenyl or naphthyl, optionally substituted by one to five groups selected in the list consisting of halogen, $[C_1-C_6]$-alkyl, $[C_1-C_6]$-haloalkyl, $[C_2-C_6]$-alkenyl, $[C_2-C_6]$-haloalkenyl, $[C_2-C_6]$-alkynyl, $[C_2-C_6]$-haloalkynyl, $[C_1-C_6]$-alkoxy, $[C_1-C_4]$-alkoxy-$[C_1-C_4]$-alkyl, $[C_1-C_4]$-alkoxy-$[C_1-C_6]$-alkoxy, $[C_1-C_6]$-haloalkoxy and $[C_1-C_4]$-haloalkoxy-$[C_1-C_4]$-alkyl;

In the case of an amino group or the amino moiety of any other amino-containing group, substituted by two substituents that can be the same or different, the two substituents together with the nitrogen atom to that they are linked can form a heterocyclyl group, preferably a 5- to 7-membered heterocyclyl group, that can be substituted or that can include other hetero atoms, for example a morpholino group or piperidinyl.

Preferred compounds of formula (I) according to the invention are those wherein A is selected in the list consisting of:

a heterocycle of formula ($A^1$)

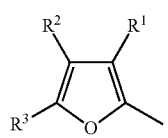

(A¹)

wherein:

$R^1$ to $R^3$ that can be the same or different represent a hydrogen atom; a halogen atom; alkyl; $C_1-C_5$-halogenoalkyl comprising up to 9 halogen atoms that can be the same or different; $C_1-C_5$-alkoxy or $C_1-C_5$-halogenoalkoxy comprising up to 9 halogen atoms that can be the same or different;

a heterocycle of formula ($A^2$)

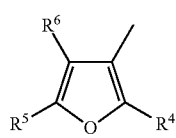

(A²)

wherein:

$R^4$ to $R^6$ that can be the same or different represent a hydrogen atom; a halogen atom; $C_1-C_5$-alkyl; $C_1-C_5$-halogenoalkyl comprising up to 9 halogen atoms that can be the same or different; $C_1-C_5$-alkoxy or $C_1-C_5$-halogenoalkoxy comprising up to 9 halogen atoms that can be the same or different;

a heterocycle of formula ($A^3$)

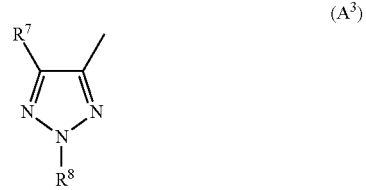

(A³)

wherein:

$R^7$ represents a hydrogen atom; a halogen atom; $C_1-C_5$-alkyl; $C_1-C_5$-halogenoalkyl comprising up to 9 halogen atoms that can be the same or different; $C_1-C_5$-alkoxy or $C_1-C_5$-halogenoalkoxy comprising up to 9 halogen atoms that can be the same or different;

$R^8$ represents a hydrogen atom or a $C_1-C_5$-alkyl;

a heterocycle of formula ($A^4$)

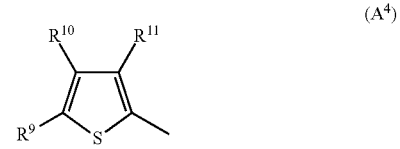

(A⁴)

wherein:

$R^9$ to $R^{11}$ that can be the same or different represent a hydrogen atom; a halogen atom; $C_1-C_5$-alkyl; amino; $C_1-C_5$-alkoxy; $C_1-C_5$-alkylsulphanyl $C_1-C_5$-halogenoalkyl comprising up to 9 halogen atoms that can be the same or different or $C_1-C_5$-halogenoalkoxy comprising up to 9 halogen atoms that can be the same or different;

a heterocycle of formula ($A^5$)

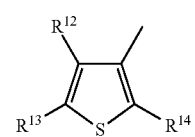

(A⁵)

wherein:

$R^{12}$ to $R^{14}$ that can be the same or different represent a hydrogen atom; a halogen atom; $C_1-C_5$-alkyl; $C_1-C_5$-alkoxy; amino; $C_1-C_5$-halogenoalkyl comprising up to 9 halogen atoms that can be the same or different or $C_1-C_5$-halogenoalkoxy comprising up to 9 halogen atoms that can be the same or different;

a heterocycle of formula ($A^6$)

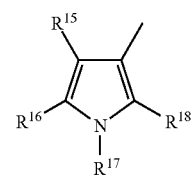

(A⁶)

wherein:

$R^{15}$ represents a hydrogen atom; a halogen atom; a cyano; $C_1$-$C_5$-alkyl; $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{16}$ and $R^{18}$ that can be the same or different represent a hydrogen atom; a halogen atom; $C_1$-$C_5$-alkoxycarbonyl; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{17}$ represents a hydrogen atom or $C_1$-$C_5$-alkyl;

a heterocycle of formula ($A^7$)

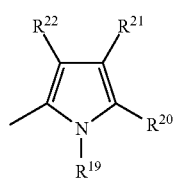

wherein:

$R^{19}$ represents a hydrogen atom or a $C_1$-$C_5$-alkyl;

$R^{20}$ to $R^{22}$ that can be the same or different represent a hydrogen atom; a halogen atom; $C_1$-$C_5$-alkyl or $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different;

a heterocycle of formula ($A^8$)

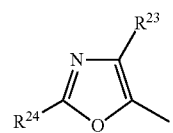

wherein:

$R^{23}$ represents a hydrogen atom; a halogen atom; $C_1$-$C_5$-alkyl or $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different;

$R^{24}$ represents a hydrogen atom or $C_1$-$C_5$-alkyl or $C_1$-$C_5$-halogenoalkyl comprising up to 9 halogen atoms that can be the same or different;

a heterocycle of formula ($A^9$)

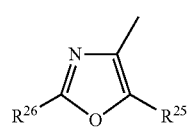

wherein:

$R^{25}$ represents a hydrogen atom; a halogen atom; $C_1$-$C_5$-alkyl or $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different;

$R^{26}$ represents a hydrogen atom; $C_1$-$C_5$-alkyl or $C_1$-$C_5$-halogenoalkyl comprising up to 9 halogen atoms that can be the same or different;

a heterocycle of formula ($A^{10}$)

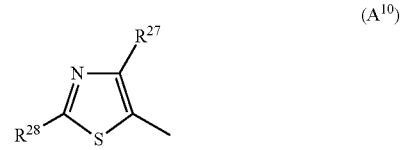

wherein:

$R^{27}$ represents a hydrogen atom; a halogen atom; $C_1$-$C_5$-alkyl or $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different;

$R^{28}$ represents a hydrogen atom; a halogen atom; amino; $C_1$-$C_5$-alkyl or $C_1$-$C_5$-halogenoalkyl comprising up to 9 halogen atoms that can be the same or different; $C_1$-$C_5$-alkoxy; C1-C5-halogenoalkoxy comprising up to 9 halogen atoms which can be the same or different; $C_1$-$C_5$-alkylsulfanyl or $C_1$-$C_5$-halogenoalkylsulfanyl comprising up to 9 halogen atoms that can be the same or different; $C_1$-$C_5$-alkylamino or di($C_1$-$C_5$-alkyl)amino;

a heterocycle of formula ($A^{11}$)

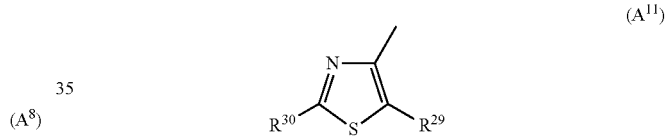

wherein:

$R^{29}$ represents a hydrogen atom; a halogen atom; $C_1$-$C_5$-alkyl; $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{39}$ represents a hydrogen atom; a halogen atom; $C_1$-$C_5$-alkyl; $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different; $C_1$-$C_5$-alkylsulfanyl or $C_1$-$C_5$-halogenoalkylsulfanyl comprising up to 9 halogen atoms that can be the same or different; amino; $C_1$-$C_5$-alkylamino or di-$C_1$-$C_5$-alkylamino;

a heterocycle of formula ($A^{12}$)

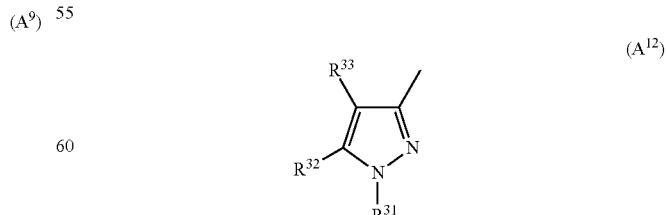

wherein:

$R^{31}$ represents a hydrogen atom; a halogen atom or a $C_1$-$C_5$-alkyl;

$R^{32}$ represents a hydrogen atom; a halogen atom; $C_1$-$C_5$-alkyl or $C_1$-$C_5$-halogenoalkyl comprising up to 9 halogen atoms that can be the same or different;

$R^{33}$ represents a hydrogen atom; a halogen atom; a nitro; $C_1$-$C_5$-alkyl; $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

a heterocycle of formula ($A^{13}$)

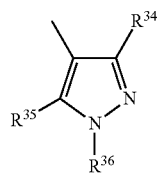

(A$^{13}$)

wherein:

$R^{34}$ represents a hydrogen atom; a halogen atom; $C_1$-$C_5$-alkyl; $C_3$-$C_5$-cycloalkyl; $C_1$-$C_5$-halogenoalkyl comprising up to 9 halogen atoms that can be the same or different; $C_1$-$C_5$-alkoxy; $C_2$-$C_5$-alkynyloxy or $C_1$-$C_5$-halogenoalkoxy comprising up to 9 halogen atoms that can be the same or different;

$R^{35}$ represents a hydrogen atom; a halogen atom; $C_1$-$C_5$-alkyl; a cyano; $C_1$-$C_5$-alkoxy; $C_1$-$C_5$-alkylsulphanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; $C_1$-$C_5$-alkylamino or di($C_1$-$C_5$-alkyl)amino;

$R^{36}$ represents a hydrogen atom or $C_1$-$C_5$-alkyl;

a heterocycle of formula ($A^{14}$)

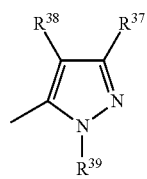

(A$^{14}$)

wherein:

$R^{37}$ and $R^{38}$ that can be the same or different represent a hydrogen atom; a halogen atom; $C_1$-$C_5$-alkyl; $C_1$-$C_5$-halogenoalkyl comprising up to 9 halogen atoms which can be the same or different; $C_1$-$C_5$-alkoxy; $C_1$-$C_5$-halogenoalkoxy comprising up to 9 halogen atoms that can be the same or different; or a $C_1$-$C_5$-alkylsulfanyl;

$R^{39}$ represents a hydrogen atom or $C_1$-$C_5$-alkyl;

a heterocycle of formula ($A^{15}$)

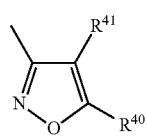

(A$^{15}$)

wherein:

$R^{40}$ and $R^{41}$ that can be the same or different represent a hydrogen atom; a halogen atom; $C_1$-$C_5$-alkyl or $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different;

a heterocycle of formula ($A^{16}$)

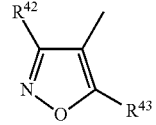

(A$^{16}$)

wherein:

$R^{42}$ and $R^{43}$ that can be the same or different represent a hydrogen atom; a halogen atom; $C_1$-$C_5$-alkyl; $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different or amino;

a heterocycle of formula ($A^{17}$)

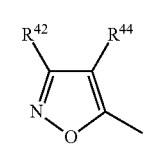

(A$^{17}$)

wherein:

$R^{44}$ and $R^{45}$ that can be the same or different represent a hydrogen atom; a halogen atom; $C_1$-$C_5$-alkyl; $C_1$-$C_5$-halogenoalkyl comprising up to 9 halogen atoms which can be the same or different; $C_1$-$C_5$-alkoxy or $C_1$-$C_5$-halogenoalkoxy comprising up to 9 halogen atoms that can be the same or different;

a heterocycle of formula ($A^{18}$)

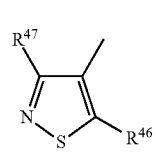

(A$^{18}$)

wherein:

$R^{47}$ represents a hydrogen atom; a halogen atom; $C_1$-$C_5$-alkyl or $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different;

$R^{46}$ represents a hydrogen atom; a halogen atom; $C_1$-$C_5$-alkyl; $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different or $C_1$-$C_5$-alkylsulphanyl;

a heterocycle of formula ($A^{19}$)

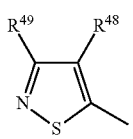
($A^{19}$)

wherein:
$R^{48}$ and $R^{49}$ that can be the same or different represent a hydrogen atom; a halogen atom; $C_1$-$C_5$-alkyl; $C_1$-$C_5$-halogenoalkyl comprising up to 9 halogen atoms that can be the same or different; $C_1$-$C_5$-alkoxy; $C_1$-$C_5$-halogenoalkyl comprising up to 9 halogen atoms that can be the same or different or $C_1$-$C_5$-alkylsulphanyl;

a heterocycle of formula ($A^{20}$)

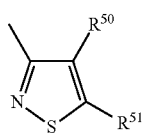
($A^{20}$)

wherein:
$R^{50}$ and $R^{51}$ that can be the same or different represent a hydrogen atom; a halogen atom; $C_1$-$C_5$-alkyl; $C_1$-$C_5$-halogenoalkyl comprising up to 9 halogen atoms that can be the same or different; $C_1$-$C_5$-alkoxy; $C_1$-$C_5$-halogenoalkyl comprising up to 9 halogen atoms that can be the same or different or $C_1$-$C_5$-alkylsulphanyl;

a heterocycle of formula ($A^{21}$)

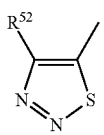
($A^{21}$)

wherein:
$R^{52}$ represents a hydrogen atom; a halogen atom; $C_1$-$C_5$-alkyl or $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different;

a heterocycle of formula ($A^{22}$)

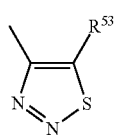
($A^{22}$)

wherein:
$R^{53}$ represents a hydrogen atom; a halogen atom; $C_1$-$C_5$-alkyl or $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different;

a heterocycle of formula ($A^{23}$)

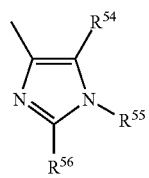
($A^{23}$)

wherein:
$R^{54}$ and $R^{55}$ that can be the same or different represent a hydrogen atom; a halogen atom; $C_1$-$C_5$-alkyl or $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different;

$R^{56}$ represents a hydrogen atom or $C_1$-$C_5$-alkyl;

a heterocycle of formula ($A^{24}$)

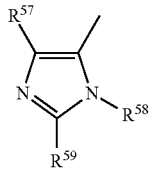
($A^{24}$)

wherein:
$R^{57}$ and $R^{59}$ that can be the same or different represent a hydrogen atom; a halogen atom; $C_1$-$C_5$-alkyl or $C_1$-$C_5$-halogenoalkyl comprising up to 9 halogen atoms that can be the same or different; $C_1$-$C_5$-alkoxy; $C_1$-$C_5$-halogenoalkoxy comprising up to 9 halogen atoms that can be the same or different;

$R^{58}$ represents a hydrogen atom or $C_1$-$C_5$-alkyl;

a heterocycle of formula ($A^{25}$)

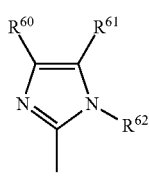
($A^{25}$)

wherein:
$R^{60}$ and $R^{61}$ that can be the same or different represent a hydrogen atom; a halogen atom; $C_1$-$C_5$-alkyl or $C_1$-$C_5$-halogenoalkyl comprising up to 9 halogen atoms that can be the same or different;

$R^{62}$ represents a hydrogen atom or $C_1$-$C_5$-alkyl;

a heterocycle of formula ($A^{26}$)

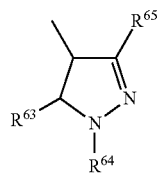

wherein:

$R^{63}$ represents a hydrogen atom; a halogen atom; $C_1$-$C_5$-alkyl; a cyano; $C_1$-$C_5$-alkoxy; $C_1$-$C_5$-alkylsulphanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; $C_1$-$C_5$-alkylamino or di($C_1$-$C_5$-alkyl)amino;

$R^{64}$ represents a hydrogen atom or $C_1$-$C_5$-alkyl;

$R^{65}$ represents a hydrogen atom; a halogen atom; $C_1$-$C_5$-alkyl; $C_3$-$C_5$-cycloalkyl; $C_1$-$C_5$-halogenoalkyl comprising up to 9 halogen atoms that can be the same or different; $C_1$-$C_5$-alkoxy; $C_2$-$C_5$-alkynyloxy or $C_1$-$C_5$-halogenoalkoxy comprising up to 9 halogen atoms that can be the same or different.

More preferred compounds of formula (I) according are those wherein A is selected in the list consisting of $A^2$; $A^6$, $A^{10}$ and $A^{13}$.

Even more preferred compounds according to the invention are those wherein A represents $A^{13}$ wherein $R^{34}$ represents $C_1$-$C_5$-alkyl $C_1$-$C_5$-halogenoalkyl comprising up to 9 halogen atoms that can be the same or different; $R^{35}$ represents a hydrogen or a fluorine atom; $R^{36}$ represents methyl.

Other preferred compounds of formula (I) according to the invention are those wherein T represents O or S.

Other more preferred compounds according to the invention are those wherein T represents O.

Other preferred compounds of formula (I) according to the invention are those wherein $Z^1$ represents cyclopropyl.

Other more preferred compounds according to the invention are those wherein those wherein $Z^1$ represents a non-substituted cyclopropyl.

Other preferred compounds of formula (I) according to the invention are those wherein $Z^2$ represents a hydrogen atom.

Other preferred compounds of formula (I) according to the invention are those wherein $L^1$ represents $CZ^4Z^5$.

Other preferred compounds of formula (I) according to the invention are those wherein $L^2$ represents $CZ^4Z^5$ and m represents 1 or 2.

Other preferred compounds of formula (I) according to the invention are those wherein $Z^3$ and $Z^7$, that can be the same or different, represent a hydrogen atom; a halogen atom; $C_1$-$C_8$-alkyl; $C_1$-$C_8$-halogenoalkyl comprising up to 9 halogen atoms that can be the same or different; $C_1$-$C_8$-alkoxy or $C_1$-$C_8$-halogenoalkoxy comprising up to 9 halogen atoms that can be the same or different.

The above mentioned preferences with regard to the substituents of the compounds of formula (I) according to the invention can be combined in various manners, either individually, partially or entirely. These combinations of preferred features thus provide sub-classes of compounds according to the invention. Examples of such sub-classes of preferred compounds according to the invention can combine:

preferred features of A with preferred features of one or more of T, $Z^1$, $Z^2$, $L^1$, $L^2$, m, $Z^3$ and $Z^7$;

preferred features of T with preferred features of one or more of A, $Z^1$, $Z^2$, $L^1$, $L^2$, m, $Z^3$ and $Z^7$;

preferred features of $Z^1$ with preferred features of one or more of A, T, $Z^2$, $L^1$, $L^2$, m, $Z^3$ and $Z^7$;

preferred features of $Z^2$ with preferred features of one or more of A, T, $Z^1$, $L^1$, $L^2$, m, $Z^3$ and $Z^7$;

preferred features of $L^1$ with preferred features of one or more of A, T, $Z^1$, $Z^2$, $L^2$, m, $Z^3$ and $Z^7$;

preferred features of $L^2$ with preferred features of one or more of A, T, $Z^1$, $Z^2$, $L^1$, m, $Z^3$ and $Z^7$;

preferred features of m with preferred features of one or more of A, T, $Z^1$, $Z^2$, $L^1$, $L^2$, $Z^3$ and $Z^7$;

preferred features of $Z^3$ with preferred features of one or more of A, T, $Z^1$, $Z^2$, $L^1$, $L^2$, m and $Z^7$;

preferred features of $Z^7$ with preferred features of one or more of A, T, $Z^1$, $Z^2$, $L^1$, $L^2$, m and $Z^3$.

In these combinations of preferred features of the substituents of the compounds according to the invention, the said preferred features can also be selected among the more preferred features of each of A, T, $Z^1$, $Z^2$, $L^1$, $L^2$, m, $Z^3$ and $Z^7$ so as to form most preferred subclasses of compounds according to the invention.

The present invention also relates to a process for the preparation of compounds of formula (I). Thus according to a further aspect of the present invention there is provided a process P1 for the preparation of a compound of formula (I) as herein-defined, as illustrated by the following reaction scheme:

Process P1

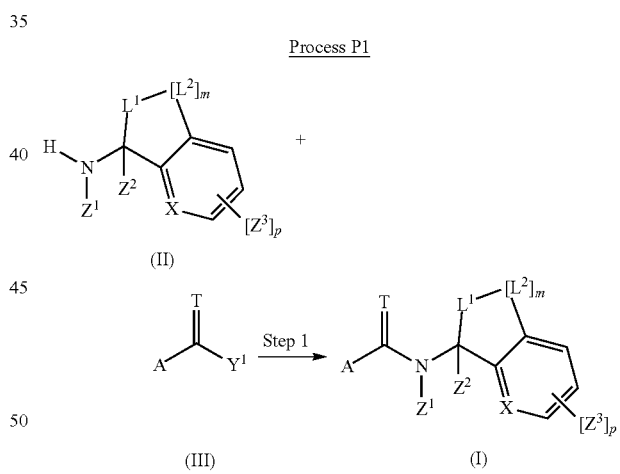

wherein

T represents O, N—$R^a$, N—$OR^a$, N—$NR^aR^b$ or N—CN;

$Y^1$ represents a halogen atom or a hydroxyl;

A, $Z^1$ to $Z^3$, $R^a$, $R^b$, $L^1$, $L^2$, X, m and p are as herein-defined

In process P1 according to the invention, step 1 can be performed if appropriate in the presence of a solvent and if appropriate in the presence of an acid binder.

N-cycloalkyl-amine derivatives of formula (II) are known or can be prepared by known processes (J. Het. Chem., 1983, p 1031-6; J. Am. Chem. Soc., 2004, p 5192-5201; Synt. Comm. 2003, p 3419-25; Chem. Pharm. Bull, 1981, 29(3), 720).

When T represents O, carboxylic acid derivatives of formula (III) are known or can be prepared by known processes (WO-93/11117; EP-A 0 545 099; Nucleosides & Nucleotides, 1987, p 737-759, Bioorg. Med. Chem., 2002, p 2105-2108).

When T represents N—$R^a$, N—$OR^a$, N—$NR^aR^b$ or N—CN, N-substituted carboximidoyl chloride derivatives of formula (III) are known or can be prepared by known processes, for example as described in Houben-Weyl, "Methoden der organischen Chemie" (1985), E5/1, 628-633 and Patai, "The chemistry of amidines and imidates" (1975), 296-301.

Suitable acid binders for carrying out process P1 according to the invention can be inorganic or organic bases which are customary for such reactions. Preference is given to using alkaline earth metal or alkali metal hydroxides, such as sodium hydroxide, calcium hydroxide, potassium hydroxide or other ammonium hydroxide derivatives; alkali metal carbonates, such as sodium carbonate, potassium carbonate, potassium bicarbonate, sodium bicarbonate; alkali metal or alkaline earth metal acetates, such as sodium acetate, potassium acetate, calcium acetate; alkaline earth metal or alkali metal hydrides, such as sodium hydride or potassium hydride; alkaline earth metal or alkali metal alcoolates, such as sodium methylate, sodium ethylate, sodium propylate or potassium t-butylate; and also tertiary amines, such as trimethylamine, triethylamine, tributylamine, N,N-dimethylaniline, pyridine, N-methylpiperidine, N,N-dimethyl-aminopyridine, diazabicyclooctane (DABCO), diazabicyclononene (DBN) or diazabicycloundecene (DBU) or a polymer-supported acid scavenger (for example as detailed in http://www.iris-biotech.de/down loads/scavengers.pdf).

It is also possible to work in the absence of any additional acid binder or to employ an excess of the amine component, so that it simultaneously acts as acid binder agent.

Suitable solvents for carrying out process P1 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone, or hexamethylphosphoric triamide; alcohols such as methanol, ethanol, propanol, iso-propanol; esters, such as methyl acetate or ethyl acetate, sulphoxides, such as dimethyl sulphoxide, or sulphones, such as sulpholane.

When carrying out process P1 according to the invention, the amine derivative of formula (II) can be employed as its salt, such as chlorhydrate or any other convenient salt.

When carrying out process P1 according to the invention, 1 mole or an excess of the amine derivative of formula (II) and from 1 to 3 moles of the acid binder can be employed per mole of the reagent of formula (III).

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that can still be present.

According to a further aspect according to the invention, there is provided a process P2 for the preparation of a compound of formula (I) wherein T represents S, as herein-defined, as illustrated by the following reaction scheme:

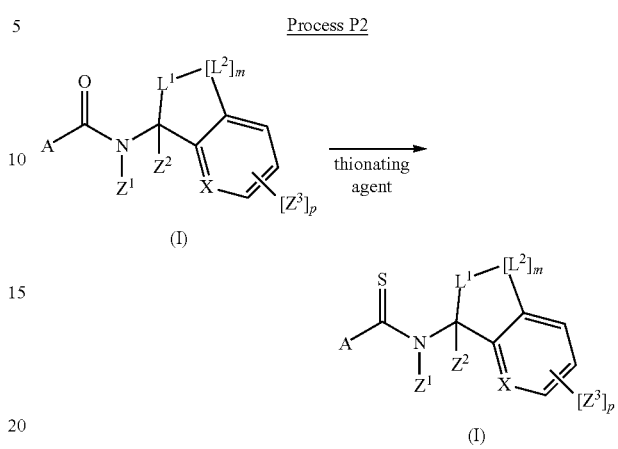

wherein A, $Z^1$ to $Z^3$, $L^1$, $L^2$, X, m, p and Y are as herein-defined;

Process P2 can be performed in the presence of a thionating agent.

Starting amide derivatives of formula (I) can be prepared according to process P1 wherein T represents O.

Suitable thionating agents for carrying out process P2 according to the invention can be sulphur (S), sulfhydric acid ($H_2S$), sodium sulfide ($Na_2S$), sodium hydrosulfide (NaHS), boron trisulfide ($B_2S_3$), bis(diethylaluminium)sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in J. Chem. Soc. Perkin 1, (2001), 358. in the presence or not of a catalytic, stoichiometric or more amount of a base such as an inorganic or organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethyl-aminopyridine or N-methylpiperidine.

Suitable solvents for carrying out process P2 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane or 1,2-diethoxyethane; nitriles, such as acetonitrile, propionitrile, n- or i-butyronitrile or benzonitrile; sulphurous solvents, such as sulpholane or carbon disulfide.

When carrying out process P2 according to the invention, 1 mole or an excess of the sulphur equivalent of the thionating agent and from 1 to 3 moles of the base can be employed per mole of the amide reactant (I).

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that can still be present.

When carrying out processes P1 and P2 according to the invention, the reaction temperatures can be varied within a relatively wide range. In general, these processes are carried out at temperatures from 0° C. to 160° C., preferably from 10° C. to 120° C. A way to control the temperature for the processes according to the invention is to use micro-wave technology.

Processes P1 and P2 according to the invention are generally carried out under atmospheric pressure. It is also possible to operate under elevated or reduced pressure.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesized.

Still in a further aspect, the present invention relates to compounds of formula (II) useful as intermediate compounds or materials for the process of preparation according to the invention. The present invention thus provides compounds of formula (II)

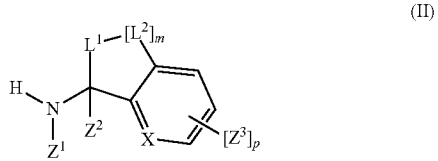

(II)

wherein $Z^1$, $Z^2$, $L^1$, $L^2$, m, X, $Z^3$ and p are as herein-defined provided that X represents N when $Z^4$ and $Z^5$ both represent a hydrogen atom or when $L^2$ represents $NZ^6$ and that compound of formula (II) is not 3-(cyclopropylamino)-2,3-dihydro-1,7-dimethyl-1H-indan-4-ol.

In a further aspect, the present invention also relates to a fungicide composition comprising an effective and non-phytotoxic amount of an active compound of formula (I).

The expression "effective and non-phytotoxic amount" means an amount of composition according to the invention that is sufficient to control or destroy the fungi present or liable to appear on the crops, and that does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials that are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with that the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active compound and/or the inert support are water-insoluble and when the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive that complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

The compounds according to the invention can also be mixed with one or more insecticide, fungicide, bactericide, attractant, acaricide or pheromone active substance or other compounds with biological activity. The mixtures thus obtained have normally a broadened spectrum of activity. The mixtures with other fungicide compounds are particularly advantageous.

Examples of suitable fungicide mixing partners can be selected in the following lists:

(1) Inhibitors of the nucleic acid synthesis, for example benalaxyl, benalaxyl-M, bupirimate, clozylacon, dimethirimol, ethirimol, furalaxyl, hymexazol, metalaxyl, metalaxyl-M, ofurace, oxadixyl and oxolinic acid.

(2) Inhibitors of the mitosis and cell division, for example benomyl, carbendazim, chlorfenazole, diethofencarb, ethaboxam, fuberidazole, pencycuron, thiabendazole, thiophanate, thiophanate-methyl and zoxamide.

(3) Inhibitors of the respiration, for example diflumetorim as CI-respiration inhibitor; bixafen, boscalid, carboxin, fenfuram, flutolanil, fluopyram, furametpyr, furmecyclox, isopyrazam (9R-component), isopyrazam (9S-component), mepronil, oxycarboxin, penthiopyrad, thifluzamide as CII-respiration inhibitor; amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyribencarb, trifloxystrobin as CIII-respiration inhibitor.

(4) Compounds capable to act as an uncoupler, like for example binapacryl, dinocap, fluazinam and meptyldinocap.

(5) Inhibitors of the ATP production, for example fentin acetate, fentin chloride, fentin hydroxide, and silthiofam.

(6) Inhibitors of the amino acid and/or protein biosynthesis, for example andoprim, blasticidin-S, cyprodinil, kasugamycin, kasugamycin hydrochloride hydrate, mepanipyrim and pyrimethanil.

(7) Inhibitors of the signal transduction, for example fenpiclonil, fludioxonil and quinoxyfen.

(8) Inhibitors of the lipid and membrane synthesis, for example biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl and vinclozolin.

(9) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, viniconazole and voriconazole.

(10) Inhibitors of the cell wall synthesis, for example benthiavalicarb, dimethomorph, flumorph, iprovalicarb, mandipropamid, polyoxins, polyoxorim, prothiocarb, validamycin A, and valiphenal.

(11) Inhibitors of the melanine biosynthesis, for example carpropamid, diclocymet, fenoxanil, phthalide, pyroquilon and tricyclazole.

(12) Compounds capable to induce a host defense, like for example acibenzolar-S-methyl, probenazole, and tiadinil.

(13) Compounds capable to have a multisite action, like for example bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxinecopper, propamidine, propineb, sulphur and sulphur preparations including calcium polysulphide, thiram, tolylfluanid, zineb and ziram.

(14) Further compounds like for example 2,3-dibutyl-6-chlorothieno[2,3-d]pyrimidin-4(3H)-one, ethyl(2Z)-3-amino-2-cyano-3-phenylprop-2-enoate, N-[2-(1,3-dimethylbutyl)phenyl]-5-fluoro-1,3-dimethyl-1H-pyrazole-4-carboxamide, N-{2-[1,1'-bi(cyclopropyl)-2-yl]phenyl}-3-(difluoromethyl)-1-methyl-1H-pyrazole-4-carboxamide, (2E)-2-(2-{[6-(3-chloro-2-methylphenoxy)-5-fluoropyrimidin-4-yl]oxy}phenyl)-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, N-(3-ethyl-3,5,5-trimethylcyclohexyl)-3-(formylamino)-2-hydroxybenzamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N-ethyl-N-methyl-N'-{2-methyl-5-(trifluoromethyl)-4-[3-(trimethylsilyl)propoxy]phenyl}imidoformamide, N'-{5-(difluoromethyl)-2-methyl-4-[3-(trimethylsilyl)propoxy]phenyl}-N-ethyl-N-methylimidoformamide, O-{1-[(4-methoxyphenoxy)methyl]-2,2-dimethylpropyl}1H-imidazole-1-carbothioate, N-[2-(4-{[3-(4-chlorophenyl)prop-2-yn-1-yl]oxy}-3-methoxyphenyl)ethyl]-N2-(methylsulfonyl)valinamide, 5-chloro-7-(4-methylpiperidin-1-yl)-6-(2,4,6-trifluorophenyl)[1,2,4]triazolo[1,5-a]pyrimidine, 5-amino-1,3,4-thiadiazole-2-thiol, propamocarb-fosetyl, 1-[(4-methoxyphenoxy)methyl]-2,2-dimethylpropyl 1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulfonyl)pyridine, 2-butoxy-6-iodo-3-propyl-4H-chromen-4-one, 2-phenylphenol and salts, 3-(difluoromethyl)-1-methyl-N-[2-(1,1,2,2-tetrafluoroethoxy)phenyl]-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, quinolin-8-ol, quinolin-8-ol sulfate (2:1) (salt), benthiazole, bethoxazin, capsimycin, carvone, chinomethionat, chloroneb, cufraneb, cyflufenamid, cymoxanil, cyprosulfamide, dazomet, debacarb, dichlorophen, diclomezine, dicloran, difenzoquat, difenzoquat methylsulphate, diphenylamine, ecomate, ferimzone, flumetover, fluopicolide, fluoroimide, flusulfamide, fosetyl-aluminium, fosetyl-calcium, fosetyl-sodium, hexachlorobenzene, irumamycin, isotianil, methasulfocarb, methyl(2E)-2-{2-[({cyclopropyl[(4-methoxyphenyl)imino]methyl}thio)methyl]phenyl}-3-methoxyacrylate, methyl isothiocyanate, metrafenone, (5-bromo-2-methoxy-4-methylpyridin-3-yl)(2,3,4-trimethoxy-6-methylphenyl)methanone, mildiomycin, tolnifanide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(Z)-[(cyclopropylmethoxy)imino][6-(difluoromethoxy)-2,3-difluorophenyl]methyl}-2-phenylacetamide, N-{(E)-[(cyclopropylmethoxy)imino][6-(difluoromethoxy)-2,3- difluorophenyl]methyl}-2-phenylacetamide, natamycin, nickel dimethyldithiocarbamate, nitrothal-isopropyl, octhilinone, oxamocarb, oxyfenthiin, pentachlorophenol and salts, phenazine-1-carboxylic acid, phenothrin, phosphorous acid and its salts, propamocarb fosetylate, propanosine-sodium, proquinazid, pyrrolnitrine, quintozene, S-prop-2-en-1-yl 5-amino-2-(1-methylethyl)-4-(2-methylphenyl)-3-oxo-2,3-dihydro-1H-pyrazole-1-carbothioate, tecloftalam, tecnazene, triazoxide, trichlamide, 5-chloro-N'-phenyl-N'-prop-2-yn-1-ylthiophene-2-sulfonohydrazide and zarilamid.

The composition according to the invention comprising a mixture of a compound of formula (I) with a bactericide compound can also be particularly advantageous. Examples of suitable bactericide mixing partners can be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compounds of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

Among the plants that may be protected by the method according to the invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rye, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots), *Elaeis* sp. (for instance oil palm); horticultural and forest crops; as well as genetically modified homologues of these crops.

Among the diseases of plants or crops that can be controlled by the method according to the invention, mention can be made of:

Powdery Mildew Diseases such as
Blumeria diseases caused for example by *Blumeria graminis*;

Podosphaera diseases caused for example by *Podosphaera leucotricha*;
Sphaerotheca diseases caused for example by *Sphaerotheca fuliginea*;
Uncinula diseases caused for example by *Uncinula necator*;
Rust Diseases such as
Gymnosporangium diseases caused for example by *Gymnosporangium sabinae*;
Hemileia diseases caused for example by *Hemileia vastatrix*;
Phakopsora diseases caused for example by *Phakopsora pachyrhizi* and *Phakopsora meibomiae*;
Puccinia diseases caused for example by *Puccinia recondite*, *Puccinia graminis* or *Puccinia striiformis*;
Uromyces diseases caused for example by *Uromyces appendiculatus*;
Oomycete Diseases such as
Albugo diseases caused for example by *Albugo candida*;
Bremia diseases caused for example by *Bremia lactucae*;
Peronospora diseases caused for example by *Peronospora pisi* and *Peronospora brassicae*;
Phytophthora diseases caused for example by *Phytophthora infestans*;
Plasmopara diseases caused for example by *Plasmopara viticola*;
Pseudoperonospora diseases caused for example by *Pseudoperonospora humuli* and *Pseudoperonospora cubensis*;
Pythium diseases caused for example by *Pythium ultimum*;
Leaf spot, Leaf blotch and Leaf Blight Diseases such as
Alternaria diseases caused for example by *Alternaria solani*;
Cercospora diseases caused for example by *Cercospora beticola*;
Cladiosporium diseases caused for example by *Cladiosporium cucumerinum*;
Cochliobolus diseases caused for example by *Cochliobolus sativus* (Conidiaform: Drechslera, Syn: Helminthosporium) or *Cochliobolus miyabeanus*;
Colletotrichum diseases caused for example by *Colletotrichum lindemuthianum*;
Cycloconium diseases caused for example by *Cycloconium oleaginum*;
Diaporthe diseases caused for example by *Diaporthe citri*;
Elsinoe diseases caused for example by *Elsinoe fawcettii*;
Gloeosporium diseases caused for example by *Gloeosporium laeticolor*;
Glomerella diseases caused for example by *Glomerella cingulata*;
Guignardia diseases caused for example by *Guignardia bidwellii*;
Leptosphaeria diseases caused for example by *Leptosphaeria maculans* and *Leptosphaeria nodorum*;
Magnaporthe diseases caused for example by *Magnaporthe grisea*;
Mycosphaerella diseases caused for example by *Mycosphaerella graminicola*, *Mycosphaerella arachidicola* and *Mycosphaerella fijiensis*;
Phaeosphaeria diseases caused for example by *Phaeosphaeria nodorum*;
Pyrenophora diseases caused for example by *Pyrenophora teres* or *Pyrenophora tritici repentis*;
Ramularia-diseases caused for example by *Ramularia collo-cygni* or *Ramularia areola*;
Rhynchosporium diseases caused for example by *Rhynchosporium secalis*;

Septoria diseases caused for example by *Septoria apii* and *Septoria lycopersici*;
Typhula diseases caused for example by *Thyphula incarnate*;
Venturia diseases caused for example by *Venturia inaequalis*;
Root-, Sheath and Stem Diseases such as
Corticium diseases caused for example by *Corticium graminearum*;
Fusarium diseases caused for example by *Fusarium oxysporum*;
Gaeumannomyces diseases caused for example by *Gaeumannomyces graminis*;
Rhizoctonia diseases caused for example by *Rhizoctonia solani*;
Sarocladium diseases caused for example by *Sarocladium oryzae*;
Sclerotium diseases caused for example by *Sclerotium oryzae*;
Tapesia diseases caused for example by *Tapesia acuformis*;
Thielaviopsis diseases caused for example by *Thielaviopsis basicola*;
Ear and Panicle Diseases including Maize cob such as
Alternaria diseases caused for example by *Alternaria* spp.;
Aspergillus diseases caused for example by *Aspergillus flavus*;
Cladosporium diseases caused for example by *Cladiosporium cladosporioides*;
Claviceps diseases caused for example by *Claviceps purpurea*;
Fusarium diseases caused for example by *Fusarium culmorum*;
Gibberella diseases caused for example by *Gibberella zeae*;
Monographella diseases caused for example by *Monographella nivalis*;
Smut- and Bunt Diseases such as
Sphacelotheca diseases caused for example by *Sphacelotheca reiliana*;
Tilletia diseases caused for example by *Tilletia caries*;
Urocystis diseases caused for example by *Urocystis occulta*;
Ustilago diseases caused for example by *Ustilago nuda*;
Fruit Rot and Mould Diseases such as
Aspergillus diseases caused for example by *Aspergillus flavus*;
Botrytis diseases caused for example by *Botrytis cinerea*;
Penicillium diseases caused for example by *Penicillium expansum* and *Penicillium purpurogenum*;
Rhizopus diseases caused by example by *Rhizopus stolonifer*
Sclerotinia diseases caused for example by *Sclerotinia sclerotiorum*;
Verticillium diseases caused for example by *Verticillium alboatrum*;
Seed- and Soilborne Decay, Mould, Wilt, Rot and Damping-off diseases
Alternaria diseases caused for example by *Alternaria brassicicola*;
Aphanomyces diseases caused for example by *Aphanomyces euteiches*;
Ascochyta diseases caused for example by *Ascochyta lentis*;
Aspergillus diseases caused for example by *Aspergillus flavus*;
Cladosporium diseases caused for example by *Cladosporium herbarum*;
Cochliobolus diseases caused for example by *Cochliobolus sativus*;
(Conidiaform: Drechslera, Bipolaris Syn: Helminthosporium);
Colletotrichum diseases caused for example by *Colletotrichum coccodes*;
Fusarium diseases caused for example by *Fusarium culmorum*;
Gibberella diseases caused for example by *Gibberella zeae*;
Macrophomina diseases caused for example by *Macrophomina phaseolina*;
Microdochium diseases caused for example by *Microdochium nivale*;
Monographella diseases caused for example by *Monographella nivalis*;
Penicillium diseases caused for example by *Penicillium expansum*;
Phoma diseases caused for example by *Phoma lingam*;
Phomopsis diseases caused for example by *Phomopsis sojae*;
Phytophthora diseases caused for example by *Phytophthora cactorum*;
Pyrenophora diseases caused for example by *Pyrenophora graminea*;
Pyricularia diseases caused for example by *Pyricularia oryzae*;
Pythium diseases caused for example by *Pythium ultimum*;
Rhizoctonia diseases caused for example by *Rhizoctonia solani*;
Rhizopus diseases caused for example by *Rhizopus oryzae*;
Sclerotium diseases caused for example by *Sclerotium rolfsii*;
Septoria diseases caused for example by *Septoria nodorum*;
Typhula diseases caused for example by *Typhula incarnate*;
Verticillium diseases caused for example by *Verticillium dahliae*;
Canker, Broom and Dieback Diseases such as
Nectria diseases caused for example by *Nectria galligena*;
Blight Diseases such as
Monilinia diseases caused for example by *Monilinia laxe*;
Leaf Blister or Leaf Curl Diseases including deformation of blooms and fruits such as
Exobasidium diseases caused for nexample by *Exobasidium vexans*.
Taphrina diseases caused for example by *Taphrina deformans*;
Decline Diseases of Wooden Plants such as
Esca disease caused for example by *Phaeomoniella clamydospora*, *Phaeoacremonium aleophilum* and *Fomitiporia mediterranea*;
Ganoderma diseases caused by example by *Ganoderma boninense*;
Diseases of Flowers and Seeds such as
Botrytis diseases caused for example by *Botrytis cinerea*;
Diseases of Tubers such as
Rhizoctonia diseases caused for example by *Rhizoctonia solani*;
Helminthosporium diseases caused for example by *Helminthosporium solani*;

Club root diseases such as

Plasmodiophora diseases, cause for example by *Plamodiophora brassicae.*

Diseases caused by Bacterial Organisms such as

*Xanthomanas* species for example *Xanthomonas campestris* pv. *oryzae;*

*Pseudomonas* species for example *Pseudomonas syringae* pv. *lachrymans;*

*Erwinia* species for example *Erwinia amylovora.*

The fungicide composition according to the invention can also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The fungicide composition according to the invention can also be used in the treatment of genetically modified organisms with the compounds according to the invention or the agrochemical compositions according to the invention. Genetically modified plants are plants into genome of that a heterologous gene encoding a protein of interest has been stably integrated. The expression "heterologous gene encoding a protein of interest" essentially means genes that give the transformed plant new agronomic properties, or genes for improving the agronomic quality of the modified plant.

The compounds or mixtures according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus.*

The various aspects of the invention will now be illustrated with reference to the following table of active or intermediate compound examples and the following preparation or efficacy examples. The following tables illustrates in a non-limiting manner examples of active or intermediate compounds according to the invention.

In the following table, M+H (or M–H) means the molecular ion peak, plus or minus 1 a.m.u. (atomic mass unit) respectively, as observed in mass spectroscopy and M (Apcl+) means the molecular ion peak as it was found via positive atmospheric pressure chemical ionisation in mass spectroscopy.

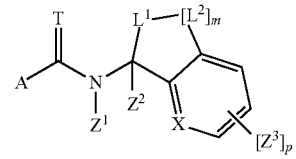

| Example | $Z^1$ | T | A | M + H | logP |
|---|---|---|---|---|---|
| 1 | | cPr | O | | 360 |
| 2 | | cPr | O | | 348 |
| 3 | | cPr | O | | 382 |

-continued

| Example | Z¹ | T | A | M + H | logP |
|---|---|---|---|---|---|
| 4 | 4,6-dichloro-indan-1-yl | cPr | S | 3-methyl-5-fluoro-1-methyl-pyrazol-4-yl | 398 | |
| 5 | 7-chloro-indan-1-yl | cPr | O | 3-methyl-5-fluoro-1-methyl-pyrazol-4-yl | 348 | |
| 6 | indan-1-yl | cPr | O | 3-methyl-5-fluoro-1-methyl-pyrazol-4-yl | 314 | |
| 7 | 4-methyl-indan-1-yl | cPr | O | 3-methyl-5-fluoro-1-methyl-pyrazol-4-yl | 328 | |
| 8 | 5-methoxy-indan-1-yl | cPr | O | 3-methyl-5-fluoro-1-methyl-pyrazol-4-yl | 344 | |
| 9 | 2-bromo-indan-1-yl | cPr | O | 3-methyl-5-fluoro-1-methyl-pyrazol-4-yl | | |
| 10 | 2-butyl-indan-1-yl | cPr | O | 3-methyl-5-fluoro-1-methyl-pyrazol-4-yl | 370 | |
| 11 | 4,7-dichloro-indan-1-yl | cPr | O | 3-methyl-5-fluoro-1-methyl-pyrazol-4-yl | 382 | |
| 12 | 2-methyl-indan-1-yl | cPr | O | 3-methyl-5-fluoro-1-methyl-pyrazol-4-yl | 328 | |

-continued

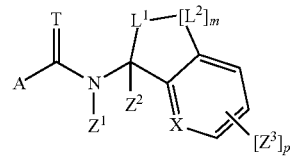

| Example | Z¹ | T | A | M + H | logP |
|---|---|---|---|---|---|
| 13 | 2,2-dimethylindanyl | cPr | O | 3-methyl-5-fluoro-1-methylpyrazol-4-yl | 342 | |
| 14 | 2,3-dihydrobenzofuran-3-yl | cPr | O | 3-methyl-5-fluoro-1-methylpyrazol-4-yl | | |
| 15 | tetralin-1-yl | cPr | O | 3-methyl-5-fluoro-1-methylpyrazol-4-yl | 328 | |
| 16 | 7-bromo-tetralin-1-yl | cPr | O | 3-methyl-5-fluoro-1-methylpyrazol-4-yl | 406 | |
| 17 | 7-bromo-tetralin-1-yl | cPr | S | 3-methyl-5-fluoro-1-methylpyrazol-4-yl | 422 | |
| 18 | 2-methyl-tetralin-1-yl | cPr | O | 3-methyl-5-fluoro-1-methylpyrazol-4-yl | | |
| 19 | 5,7-dimethyl-tetralin-1-yl | cPr | O | 3-methyl-5-fluoro-1-methylpyrazol-4-yl | 356 | |
| 20 | 3,3-dichloro-tetralin-1-yl | cPr | O | 3-methyl-5-fluoro-1-methylpyrazol-4-yl | | |

-continued

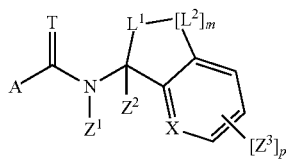

| Example | Z¹ | T | A | M + H | logP |
|---|---|---|---|---|---|
| 21 | (1,1-dimethyl-tetrahydronaphthalen-4-yl) | cPr | O | 3-methyl-5-fluoro-1-methyl-pyrazol-4-yl | 356 | |
| 22 | (6-isopropoxy-tetrahydronaphthalen-1-yl) | cPr | O | 3-methyl-5-fluoro-1-methyl-pyrazol-4-yl | 386 | |
| 23 | (2-bromo-tetrahydronaphthalen-1-yl) | cPr | O | 3-methyl-5-fluoro-1-methyl-pyrazol-4-yl | | |
| 24 | (5,6,7,8-tetrahydroquinolin-8-yl) | cPr | O | 3-methyl-5-fluoro-1-methyl-pyrazol-4-yl | 329 | |
| 25 | (chroman-4-yl) | cPr | O | 3-methyl-5-fluoro-1-methyl-pyrazol-4-yl | 330 | |
| 26 | (thiochroman-4-yl) | cPr | O | 3-methyl-5-fluoro-1-methyl-pyrazol-4-yl | 346 | |
| 27 | (3,3-dimethyl-6,7-dimethoxy-chroman-4-yl) | cPr | O | 3-methyl-5-fluoro-1-methyl-pyrazol-4-yl | | |
| 28 | (6-chloro-chroman-4-yl) | cPr | O | 3-methyl-5-fluoro-1-methyl-pyrazol-4-yl | 364 | |

-continued

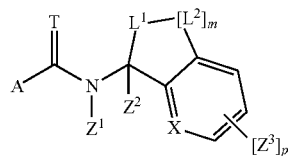

| Example | Z¹ | T | A | M + H | logP |
|---|---|---|---|---|---|
| 29 | [6-chloro-benzoxathiine-2,2-dioxide] | cPr | O | [3-methyl-5-fluoro-1-methylpyrazole] | | |
| 30 | [8-bromo-tetrahydronaphthalene] | cPr | O | [3-methyl-5-fluoro-1-methylpyrazole] | 406 | |
| 31 | [7-phenyl-tetrahydronaphthalene] | cPr | O | [3-methyl-5-fluoro-1-methylpyrazole] | 404 | |
| 32 | [7-(2,4-dichlorobenzyloxy)-tetrahydronaphthalene] | cPr | O | [3-methyl-5-fluoro-1-methylpyrazole] | 502 | |
| 33 | [7-(2,4-difluorobenzyloxy)-tetrahydronaphthalene] | cPr | O | [3-methyl-5-fluoro-1-methylpyrazole] | 470 | |
| 34 | [7-(pyridin-3-yl)-tetrahydronaphthalene] | cPr | O | [3-methyl-5-fluoro-1-methylpyrazole] | 405 | |
| 35 | [7-benzyloxy-tetrahydronaphthalene] | cPr | O | [3-methyl-5-fluoro-1-methylpyrazole] | 434 | |
| 36 | [thiochromane-1,1-dioxide] | cPr | O | [3-methyl-5-fluoro-1-methylpyrazole] | 378 | |

-continued
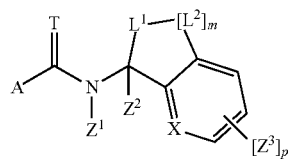
| Example | Z¹ | T | A | M + H | logP |
|---|---|---|---|---|---|
| 37 | 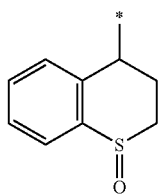 | cPr O | 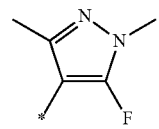 | 362 | |
| 38 | 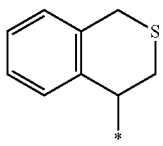 | cPr O | 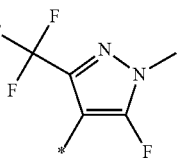 | 400 | |
| 39 | 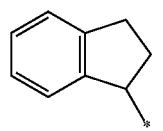 | cPr O | 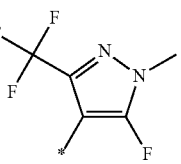 | 368 | |
| 40 | 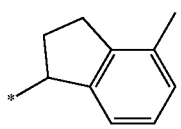 | cPr O | 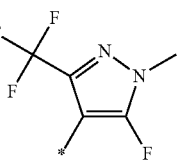 | 382 | |
| 41 | 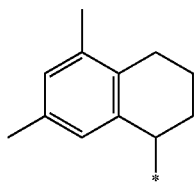 | cPr O | 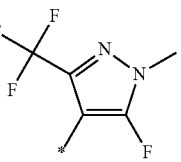 | 410 | |
| 42 | 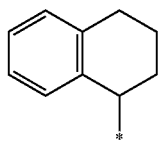 | cPr O | 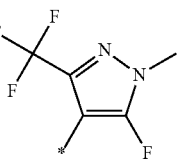 | 382 | |
| 43 | 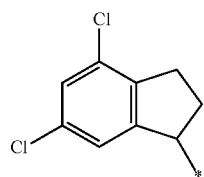 | cPr O | 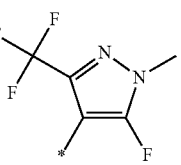 | 436 | |

-continued
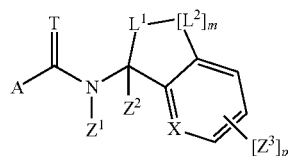
| Example | Z¹ | T | A | M + H | logP |
|---|---|---|---|---|---|
| 44 | 4-Cl-indan-1-yl | cPr | O | 3-CF3-5-F-1-Me-pyrazol-4-yl | 402 | |
| 45 | 5-Cl-indan-1-yl | cPr | O | 3-CF3-5-F-1-Me-pyrazol-4-yl | 402 | |
| 46 | 7-Br-tetralin-1-yl | cPr | O | 3-CF3-5-F-1-Me-pyrazol-4-yl | 460 | |
| 47 | 7-F-benzosuberan-5-yl | cPr | O | 3-CF3-5-F-1-Me-pyrazol-4-yl | 414 | |
| 48 | 6-MeO-indan-1-yl | cPr | O | 3-CF3-5-F-1-Me-pyrazol-4-yl | 398 | |
| 49 | chroman-4-yl | cPr | O | 3-CF3-5-F-1-Me-pyrazol-4-yl | 384 | |
| 50 | thiochroman-4-yl | cPr | O | 3-CF3-5-F-1-Me-pyrazol-4-yl | 400 | |
| 51 | 2-Me-indan-1-yl | cPr | O | 3-CF3-5-F-1-Me-pyrazol-4-yl | 382 | |

-continued
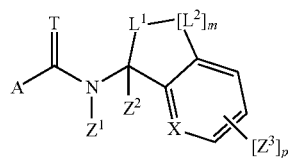
| Example | Z¹ | T | A | M + H | logP |
|---|---|---|---|---|---|
| 52 | 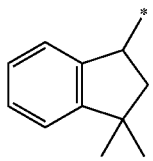 | cPr O | 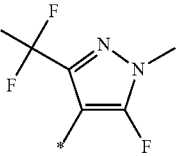 | 396 | |
| 53 | 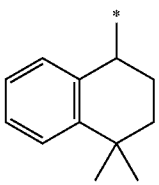 | cPr O | 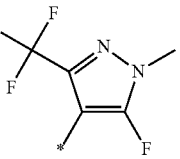 | 410 | |
| 54 | 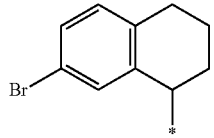 | cPr O | 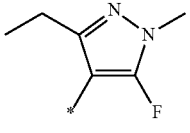 | 420 | |
| 55 | 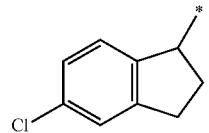 | cPr O | 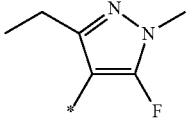 | 362 | |
| 56 | 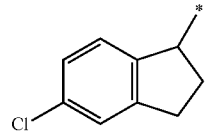 | cPr S | 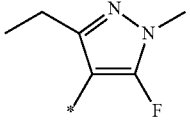 | 378 | |
| 57 | 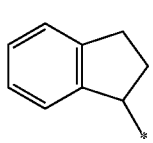 | cPr O | 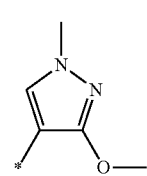 | 312 | |
| 58 | 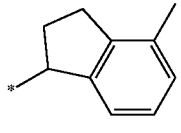 | cPr O | 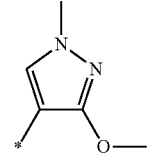 | 326 | |
| 59 | 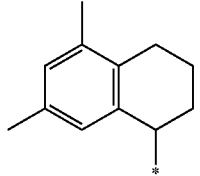 | cPr O | 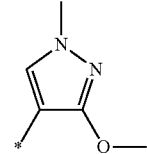 | 354 | |

-continued
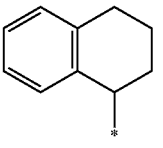
| Example | Z¹ | T | A | M + H | logP |
|---|---|---|---|---|---|
| 60 | 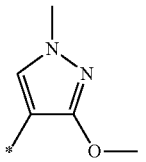 | cPr O | 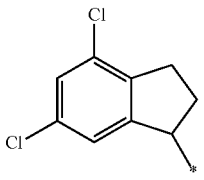 | 326 | |
| 61 | 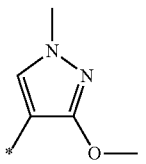 | cPr O | 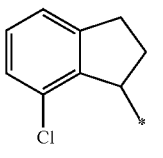 | 380 | |
| 62 | 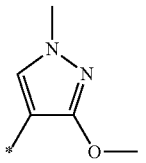 | cPr O | 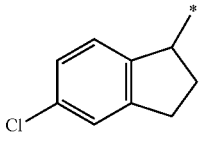 | 346 | |
| 63 | 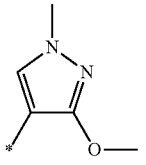 | cPr O | 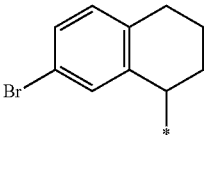 | 346 | |
| 64 | 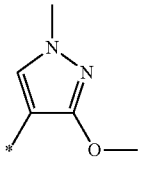 | cPr O | 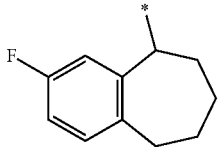 | 404 | |
| 65 | 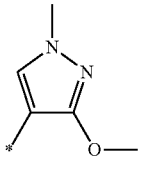 | cPr O | 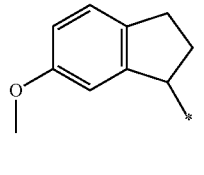 | 358 | |
| 66 | 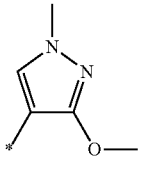 | cPr O | 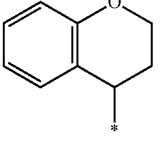 | 342 | |
| 67 | 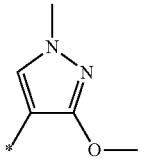 | cPr O | | 328 | |

-continued

| Example | Z¹ | T | A | M + H | logP |
|---|---|---|---|---|---|
| 68 | thiochroman-4-yl | cPr | O | 1-methyl-3-methoxy-pyrazol-4-yl | 344 | |
| 69 | isothiochroman-4-yl | cPr | O | 1-methyl-3-methoxy-pyrazol-4-yl | 344 | |
| 70 | 2-methyl-indan-1-yl | cPr | O | 1-methyl-3-methoxy-pyrazol-4-yl | 326 | |
| 71 | 3,3-dimethyl-indan-1-yl | cPr | O | 1-methyl-3-methoxy-pyrazol-4-yl | 340 | |
| 72 | 4,4-dimethyl-tetralin-1-yl | cPr | O | 1-methyl-3-methoxy-pyrazol-4-yl | 354 | |
| 73 | 7-fluoro-benzosuberan-5-yl | cPr | O | 1-methyl-3-difluoromethyl-pyrazol-4-yl | 378 | |
| 74 | 5-chloro-indan-1-yl | cPr | O | 1-methyl-3-difluoromethyl-pyrazol-4-yl | 366 | |
| 75 | 4,6-dichloro-indan-1-yl | cPr | O | 1-methyl-3-difluoromethyl-pyrazol-4-yl | 400 | |

-continued
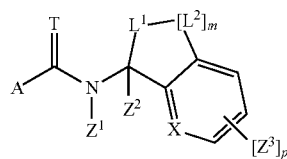
| Example | Z¹ | T | A | M + H | logP |
|---|---|---|---|---|---|
| 76 | 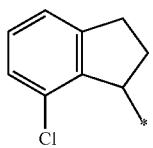 | cPr | O | 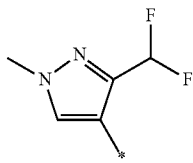 | 366 | |
| 77 | 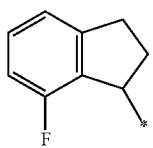 | cPr | S | 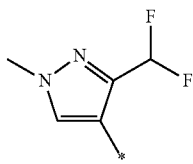 | | |
| 78 | 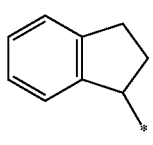 | cPr | O | 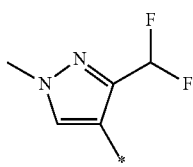 | 332 | |
| 79 | 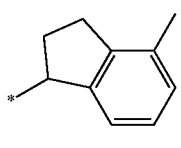 | cPr | O | 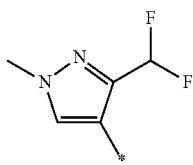 | 346 | |
| 80 | 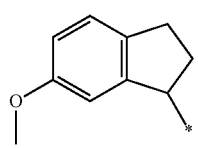 | cPr | O | 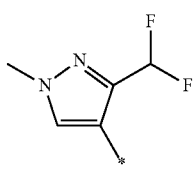 | 362 | |
| 81 | 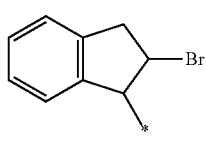 | cPr | O | 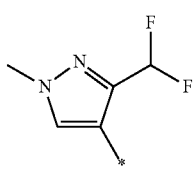 | 410 | |
| 82 | 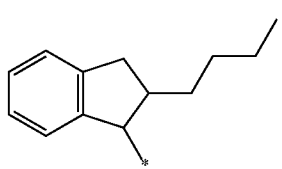 | cPr | O | 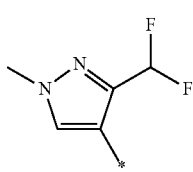 | 388 | |

-continued
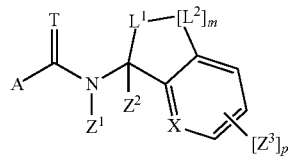
| Example | Z¹ | T | A | M + H | logP |
|---|---|---|---|---|---|
| 83 | 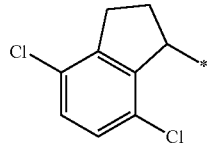 | cPr | O | 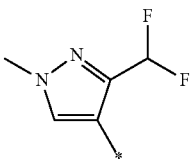 | 400 | |
| 84 | 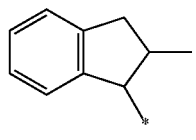 | cPr | O | 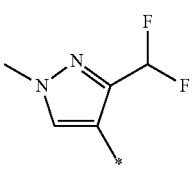 | 346 | |
| 85 | 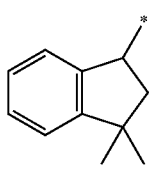 | cPr | O | 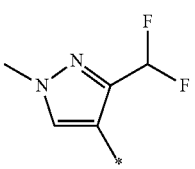 | 360 | |
| 86 | 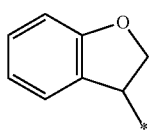 | cPr | O | 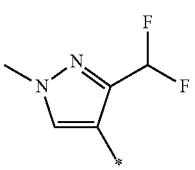 | | |
| 87 | 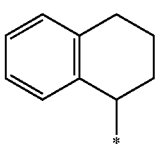 | cPr | O | 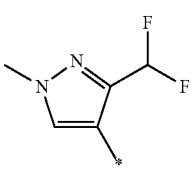 | 346 | |
| 88 | 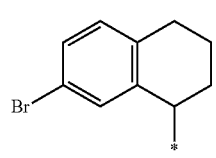 | cPr | O | 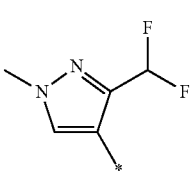 | 424 | |
| 89 | 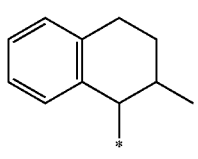 | cPr | O | 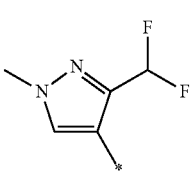 | | |

-continued
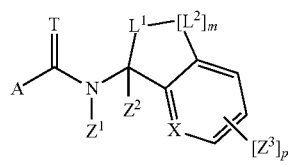
| Example | Z¹ | T | A | M + H | logP |
|---|---|---|---|---|---|
| 90 | 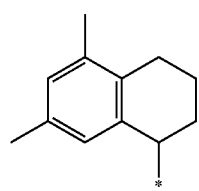 | cPr | O | 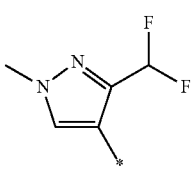 | 374 |
| 91 | 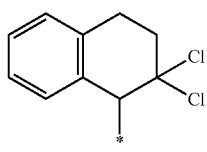 | cPr | O | 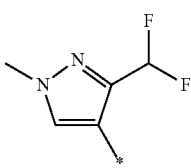 | |
| 92 | 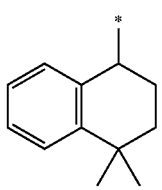 | cPr | O | 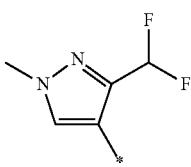 | 374 |
| 93 | 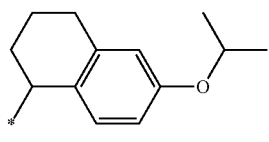 | cPr | O | 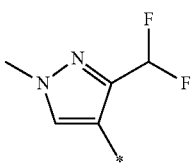 | |
| 94 | 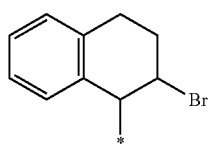 | cPr | O | 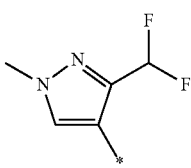 | |
| 95 | 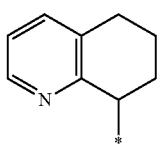 | cPr | O | 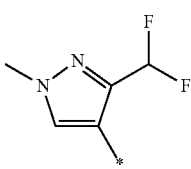 | 347 |
| 96 | 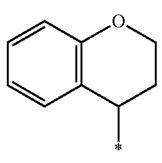 | cPr | O | 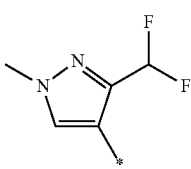 | 348 |

-continued

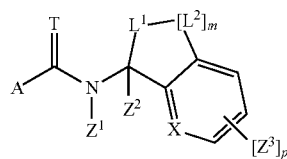

| Example | Z¹ | T | A | M + H | logP |
|---|---|---|---|---|---|
| 97 | (thiochroman-4-yl) | cPr | O | (1-methyl-3-difluoromethyl-pyrazol-4-yl) | 364 | |
| 98 | (2,2-dimethyl-6,7-dimethoxychroman-4-yl) | cPr | O | (1-methyl-3-difluoromethyl-pyrazol-4-yl) | 436 | |
| 99 | (6-chlorochroman-4-yl) | cPr | O | (1-methyl-3-difluoromethyl-pyrazol-4-yl) | 382 | |
| 100 | (benzoxathiine-2,2-dioxide-4-yl) | cPr | O | (1-methyl-3-difluoromethyl-pyrazol-4-yl) | | |
| 101 | (isothiochroman-4-yl) | cPr | O | (1-methyl-3-difluoromethyl-pyrazol-4-yl) | 364 | |
| 102 | (7-(2,4-dichlorobenzyloxy)-tetralin-1-yl) | cPr | O | (1-methyl-3-difluoromethyl-pyrazol-4-yl) | 520 | |
| 103 | (7-(2,4-difluorobenzyloxy)-tetralin-1-yl) | cPr | O | (1-methyl-3-difluoromethyl-pyrazol-4-yl) | 488 | |

-continued

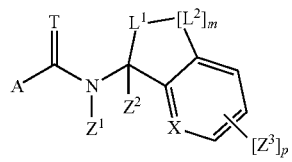

| Example | Z¹ | T | A | M + H | logP |
|---|---|---|---|---|---|
| 104 | 6-methoxy-tetrahydronaphthalenyl | cPr | O | 1-methyl-3-(difluoromethyl)pyrazol-4-yl | 376 | |
| 105 | 7-benzyloxy-tetrahydronaphthalen-5-yl | cPr | O | 1-methyl-3-(difluoromethyl)pyrazol-4-yl | 452 | |
| 106 | 8-bromo-tetrahydronaphthalen-1-yl | cPr | O | 1-methyl-3-(difluoromethyl)pyrazol-4-yl | 424 | |
| 107 | 5-chloro-indan-1-yl | cPr | O | 1-methyl-3-ethylpyrazol-4-yl | 344 | |
| 108 | 7-bromo-tetrahydronaphthalen-1-yl | cPr | O | 1-methyl-3-ethylpyrazol-4-yl | 402 | |
| 109 | 7-phenyl-tetrahydronaphthalen-1-yl | cPr | O | 1-methyl-3-(difluoromethyl)pyrazol-4-yl | | |
| 110 | 6-chloro-benzoxathiine-S,S-dioxide-4-yl | cPr | O | 1-methyl-3-(difluoromethyl)pyrazol-4-yl | | |
| 111 | 7-(pyridin-3-yl)-tetrahydronaphthalen-1-yl | cPr | O | 1-methyl-3-(difluoromethyl)pyrazol-4-yl | | |

-continued
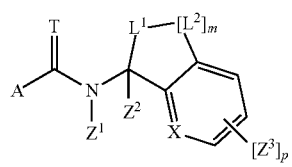
| Example | Z¹ | T | A | M + H | logP |
|---|---|---|---|---|---|
| 112 | 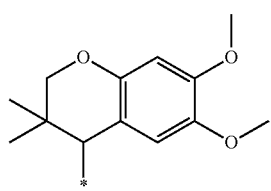 | cPr O | 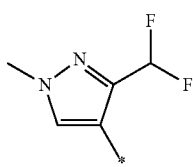 | | |
| 113 | 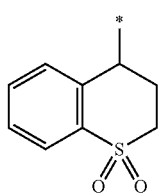 | cPr O | 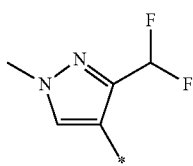 | | |
| 114 | 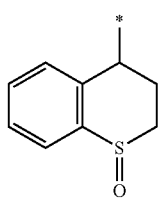 | cPr O | 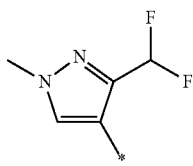 | | |
| 115 | 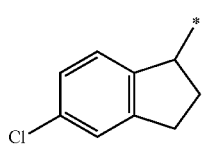 | cPr O | 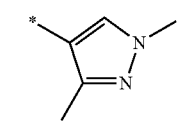 | 330 | |
| 116 | 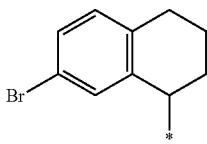 | cPr O | 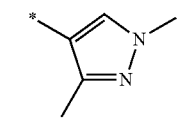 | 388 | |
| 117 | 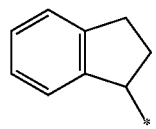 | cPr O | 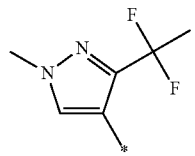 | 350 | |
| 118 | 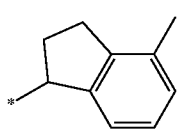 | cPr O | 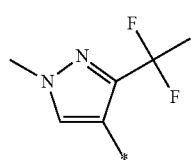 | 364 | |

-continued
| Example | Z¹ | T | A | M + H | logP |
|---|---|---|---|---|---|
| 119 | 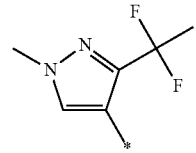 | cPr O | 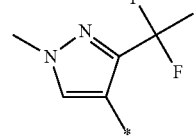 | 392 | |
| 120 | 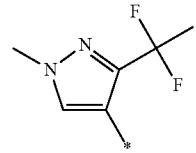 | cPr O | | 364 | |
| 121 | 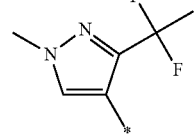 | cPr O | | 418 | |
| 122 | 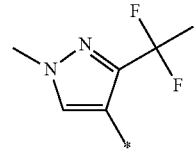 | cPr O | | 384 | |
| 123 | 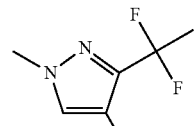 | cPr O | | 384 | |
| 124 | 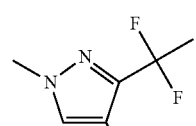 | cPr O | | 442 | |
| 125 | 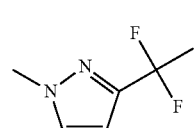 | cPr O | | 396 | |
| 126 | | cPr O | | 380 | |

-continued

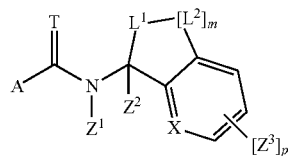

| Example | Z¹ | T | A | M + H | logP |
|---|---|---|---|---|---|
| 127 | chroman-4-yl | cPr | O | 1-methyl-3-(1,1-difluoroethyl)pyrazol-4-yl | 366 | |
| 128 | thiochroman-4-yl | cPr | O | 1-methyl-3-(1,1-difluoroethyl)pyrazol-4-yl | 382 | |
| 129 | isothiochroman-4-yl | cPr | O | 1-methyl-3-(trifluoromethyl)pyrazol-4-yl | 382 | |
| 130 | 2-methylindan-1-yl | cPr | O | 1-methyl-3-(trifluoromethyl)pyrazol-4-yl | 364 | |
| 131 | 3,3-dimethylindan-1-yl | cPr | O | 1-methyl-3-(trifluoromethyl)pyrazol-4-yl | 378 | |
| 132 | 4,4-dimethyltetralin-1-yl | cPr | O | 1-methyl-3-(trifluoromethyl)pyrazol-4-yl | 392 | |
| 133 | indan-1-yl | cPr | O | 1-methyl-3-(trifluoromethyl)pyrazol-4-yl | 349 | |
| 134 | 7-methylindan-1-yl | cPr | O | 1-methyl-3-(trifluoromethyl)pyrazol-4-yl | 363 | |

-continued
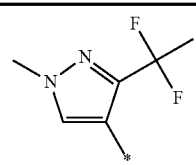
| Example | Z¹ | T | A | M + H | logP |
|---|---|---|---|---|---|
| 135 | 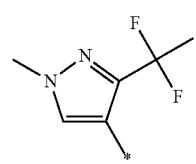 | cPr O | 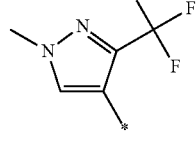 | 391 | |
| 136 | 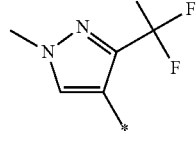 | cPr O | 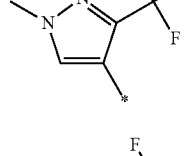 | 363 | |
| 137 | 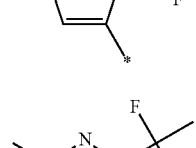 | cPr O | 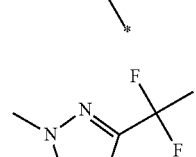 | 417 | |
| 138 |  | cPr O | | 383 | |
| 139 | | cPr O | | 383 | |
| 140 | | cPr O | | 441 | |
| 141 | | cPr O | | 395 | |
| 142 | | cPr O | | 379 | |

-continued

| Example | Z¹ | T | A | M + H | logP |
|---|---|---|---|---|---|
| 143 | chroman-4-yl | cPr | O | 1-methyl-3-(trifluoromethyl)-1H-pyrazol-4-yl | 365 | |
| 144 | thiochroman-4-yl | cPr | O | 1-methyl-3-(trifluoromethyl)-1H-pyrazol-4-yl | 381 | |
| 145 | isothiochroman-4-yl | cPr | O | 1-methyl-3-(trifluoromethyl)-1H-pyrazol-4-yl | 381 | |
| 146 | 2-methylindan-1-yl | cPr | O | 1-methyl-3-(trifluoromethyl)-1H-pyrazol-4-yl | 363 | |
| 147 | 3,3-dimethylindan-1-yl | cPr | O | 1-methyl-3-(trifluoromethyl)-1H-pyrazol-4-yl | 377 | |
| 148 | 4,4-dimethyltetralin-1-yl | cPr | O | 1-methyl-3-(trifluoromethyl)-1H-pyrazol-4-yl | 391 | |
| 149 | 5-chloroindan-1-yl | cPr | O | 2,5-dimethylfuran-3-yl | 330 | |
| 150 | 5-chloroindan-1-yl | cPr | O | 2,5-dimethylfuran-3-yl | | |

-continued

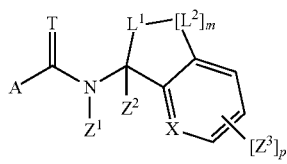

| Example | Z¹ | T | A | M + H | logP |
|---|---|---|---|---|---|
| 151 | (6-bromo-tetralin-1-yl) | cPr | O | 2,5-dimethylfuran-3-yl | 388 | |
| 152 | (3,3-dimethyl-indan-1-yl) | cPr | O | 2-methyl-4-(trifluoromethyl)thiazol-5-yl | 395 | |
| 153 | (4-methyl-indan-1-yl) | cPr | O | 2-methyl-4-(trifluoromethyl)thiazol-5-yl | 381 | |
| 154 | (5-chloro-indan-1-yl) | cPr | O | 2-methyl-4-(trifluoromethyl)thiazol-5-yl | 401 | |
| 155 | (6-methoxy-indan-1-yl) | cPr | O | 2-methyl-4-(trifluoromethyl)thiazol-5-yl | 397 | |
| 156 | (indan-1-yl) | cPr | O | 2-methyl-4-(trifluoromethyl)thiazol-5-yl | 367 | |
| 157 | (7-chloro-indan-1-yl) | cPr | O | 2-methyl-4-(trifluoromethyl)thiazol-5-yl | 401 | |
| 158 | (2-methyl-indan-1-yl) | cPr | O | 2-methyl-4-(trifluoromethyl)thiazol-5-yl | 381 | |

-continued
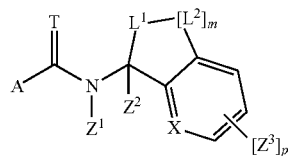
| Example | Z¹ | T | A | M + H | logP |
|---|---|---|---|---|---|
| 159 | 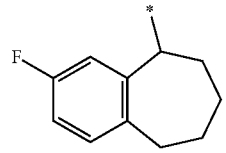 | cPr O | 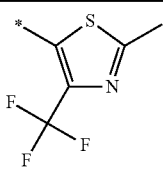 | 413 | |
| 160 | 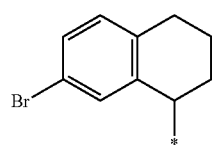 | cPr O | 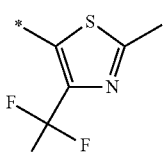 | 459 | |
| 161 | 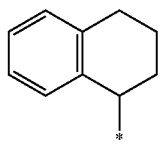 | cPr O | 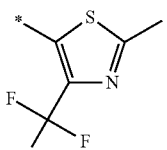 | 381 | |
| 162 | 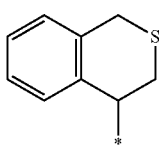 [SMILES: *C1CSCc2ccccc21] | cPr O | 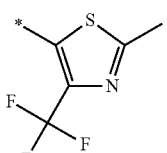 | 399 | |
| 163 | 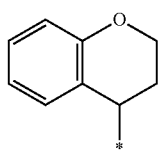 | cPr O | 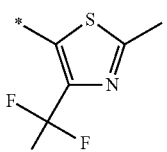 | 383 | |
| 164 | 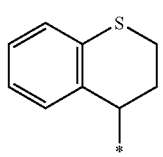 [SMILES: *C1CCSc2ccccc21] | cPr O | 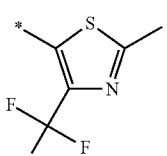 | 399 | |

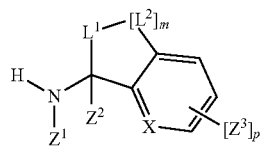
| Example | | Z¹ | M + H | logP |
|---|---|---|---|---|
| 165 | (isothiochroman-4-yl) | cPr | 206 | |
| 166 | (5,6,7,8-tetrahydroquinolin-8-yl) | cPr | 189 | |
| 167 | (6,7-dimethoxy-3,3-dimethylchroman-4-yl) | cPr | | 1.22 |
| 168 | (7-((2,4-dichlorobenzyl)oxy)-1,2,3,4-tetrahydronaphthalen-1-yl) | cPr | 362 | |
| 169 | (7-(benzyloxy)-1,2,3,4-tetrahydronaphthalen-1-yl) | cPr | 294 | |
| 170 | (7-((2,4-difluorobenzyl)oxy)-1,2,3,4-tetrahydronaphthalen-1-yl) | cPr | 330 | |
| 171 | (2-methyl-2,3-dihydro-1H-inden-1-yl) | cPr | | 0.81 |
| 172 | (2-butyl-2,3-dihydro-1H-inden-1-yl) | cPr | 230 | |

-continued

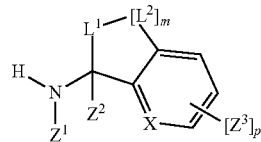

| Example | Z¹ | M + H | logP |
|---|---|---|---|
| 173 | (2-bromo-indanyl) | cPr | 252 |
| 174 | (3,3-dimethyl-indanyl) | cPr | | 1.15 |
| 175 | (chroman-4-yl) | cPr | | 0.32 |
| 176 | (6-chloro-chroman-4-yl) | cPr | | 0.83 |
| 177 | (thiochroman-4-yl) | cPr | | 0.67 |
| 178 | (4,4-dimethyl-tetralin-1-yl) | cPr | | 1.26 |

The following examples illustrate in a non-limiting manner the preparation and efficacy of the compounds of formula (I) according to the invention.

PREPARATION EXAMPLE

N-(7-chloro-2,3-dihydro-1H-inden-1-yl)-N-cyclopropyl-5-fluoro-1,3-dimethyl-1H-pyrazole-4-carboxamide (compound 5)

Step 1: preparation of 7-chloro-N-cyclopropyl-2,3-dihydro-1H-inden-1-amine

To a cooled solution of 4.16 ml (60 mmol) of cyclopropylamine and 4.3 ml (75 mmol) of acetic acid, together with 5 g of 3 Å molecular sieves, in 80 ml of methanol, are added 5 g (30 mmol) of 7-chloro-2,3-dihydro-1H-inden-1-one. The reaction mixture is stirred for 4 hrs at reflux. The reaction mixture is then cooled to ambient temperature and 2.83 g (45 mmol) of sodium cyanoborohydride are slowly added. The reaction mixture is further stirred for 2 hrs at reflux. The solvent is removed under vacuum and 100 ml of water are then added to the residue and the pH is adjusted to 10 with sodium hydroxide. The watery layer is extracted three times with dichloromethane (3×50 ml); the combined organic layers are dried over magnesium sulphate and concentrated in vacuum to yield 5.6 g (80% yield) of 7-chloro-N-cyclopropyl-2,3-dihydro-1H-inden-1-amine as an brown oil (M+1=208).

Step 2: preparation of N-(7-chloro-2,3-dihydro-1H-inden-1-yl)-N-cyclopropyl-5-fluoro-1,3-dimethyl-1H-pyrazole-4-carboxamide At ambient temperature, a solution of 0.19 g (1.06 mmol) of 5-fluoro-1,3-dimethyl-1H-pyrazole-4-carbonyl chloride in 3 ml of tetrahydrofurane is added dropwise to a solution of 0.20 g (0.96 mmol) of 7-chloro-N-cyclopropyl-2,3-dihydro-1H-inden-1-amine and 0.15 ml triethylamine in 8 ml tetrahydrofurane. The reaction mixture is stirred for 3 hrs at reflux. The solvent is removed under vacuum and 10 ml of water are then added to the residue. The watery layer is extracted three times with ethyl acetate (3×20 ml); the combined organic layers are dried over magnesium sulphate and concentrated in vacuum. Column chromatography (gradient n-heptane/ethyl acetate) yields 0.26 mg (73% yield) of N-(7-chloro-2,3-dihydro-1H-inden-1-yl)-N-cyclopropyl-5-fluoro-1,3-dimethyl-1H-pyrazole-4-carboxamide as an orange oil (M+1=348).

General Preparation Example

Thionation of Amide of Formula (I) on Chemspeed Apparatus

In a 13 ml Chemspeed vial is weighted 0.27 mmole of phosphorous pentasulfide ($P_2S_5$). 3 ml of a 0.18 molar solution of the amide (I) (0.54 mmole) in dioxane is added and the mixture is heated at reflux for two hours. The temperature is then cooled to 80° C. and 2.5 ml of water are added. The mixture is heated at 80° C. for one more hour. 2 ml of water are then added and the reaction mixture is extracted twice by 4 ml of dichloromethane. The organic phase is deposited on a basic alumina cartridge (2 g) and eluted twice by 8 ml of dichloromethane. The solvents are removed and the crude thioamide derivative is analyzed by LCMS and NMR. Insufficiently pure compounds are further purified by preparative LCMS.

Example A

In Vivo Test on *Pyrenophora teres* (Barley Net Blotch)

The active ingredients tested are prepared by homogenization in a mixture of acetone/tween/DMSO, then diluted with water to obtain the desired active material concentration.

Barley plants (Express variety), sown on a 50/50 peat soil-pozzolana substrate in starter cups and grown at 12° C., are treated at the 1-leaf stage (10 cm tall) by spraying with the active ingredient prepared as described above. Plants, used as controls, are treated with the mixture of acetone/tween/DMSO/water not containing the active material.

After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants. Under these conditions, good (at least 70%) or total protection is observed at a dose of 500 ppm with the following compounds: 1, 2, 3, 4, 5, 6, 8, 10, 11, 12, 13, 15, 16, 17, 19, 25, 28, 32, 35, 39, 40, 42, 43, 44, 45, 46, 47, 48, 49, 51, 52, 54, 55, 56, 62, 63, 64, 65, 69, 73, 74, 75, 76, 78, 79, 80, 81, 82, 83, 84, 85, 87, 90, 92, 95, 105, 117, 122, 125, 133, 134, 136, 137, 138, 139 and 141.

Example B

In Vivo Test on *Mycosphaerella qraminicola* (Wheat Leaf Spot)

The active ingredients tested are prepared by homogenization in a mixture of acetone/tween/DMSO, then diluted with water to obtain the desired active material concentration.

Wheat plants (Scipion variety), sown on a 50/50 peat soil-pozzolana substrate in starter cups and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Mycosphaerella graminicola* spores (500 000 spores per ml). The spores are collected from a 7-day-old culture. The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

Under these conditions, good (at least 70%) or total protection is observed at a dose of 500 ppm with the following compounds: 1, 2, 3, 5, 6, 7, 8, 10, 15, 16, 19, 22, 24, 30, 31, 34, 35, 39, 40, 41, 42, 43, 44, 45, 46, 48, 49, 50, 51, 52, 53, 56, 57, 58, 59, 60, 62, 63, 65, 66, 68, 70, 72, 73, 74, 75, 76, 78, 80, 81, 83, 84, 87, 88, 90, 95, 102, 103, 105, 106, 107, 115, 116, 117, 118, 119, 121, 122, 123, 130, 131, 132, 133, 134, 136, 137, 138, 139, 140, 141, 142, 143, 144, 145, 146, 147, 148, 153 and 157.

Example C

In Vivo Test on *Puccinia recondita* (Brown Rust)

The active ingredients tested are prepared by homogenization in a mixture of acetone/tween/DMSO, then diluted with water to obtain the desired active material. Wheat plants (Scipion variety) sown on 50/50 peat soil-pozzolana substrate in starter cups and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by spraying the leaves with an aqueous suspension of *Puccinia recondita* spores (100,000 spores per ml). The spores are collected from a 10-day-old contaminated wheat and are suspended in water containing 2.5 ml/l of tween 80 10%. The contaminated wheat plants are incubated for 24 hours at 20° C. and at 100% relative humidity, and then for 10 days at 20° C. and at 70% relative humidity.

Grading is carried out 10 days after the contamination, in comparison with the control plants. Under these conditions, good (at least 70%) or total protection is observed at a dose of 500 ppm with the following compounds: 1, 2, 3, 4, 6, 7, 8, 10, 11, 12, 13, 15, 16, 17, 19, 22, 25, 26, 28, 30, 31, 33, 34, 35, 41, 42, 46, 47, 51, 53, 54, 55, 59, 65, 72, 73, 75, 84, 85, 87, 88, 90, 92, 96, 99, 101, 104, 106, 108, 116, 141, 149 and 151.

Example D

In Vivo Test on *Alternaria brassicae* (Leaf Spot of Crucifers)

The active ingredients tested are prepared by potter homogenization in a mixture of acetone/tween/water. This suspension is then diluted with water to obtain the desired active material concentration.

Radish plants (Pernot variety), sown on a 50/50 peat soil-pozzolana substrate in starter cups and grown at 18-20° C., are treated at the cotyledon stage by spraying with the active ingredient prepared as described above.

Plants, used as controls, are treated with the mixture of acetone/tween/water not containing the active material.

After 24 hours, the plants are contaminated by spraying them with an aqueous suspension of *Alternaria brassicae* spores (40,000 spores per cm$^3$). The spores are collected from a 12 to 13 days-old culture.

The contaminated radish plants are incubated for 6-7 days at about 18° C., under a humid atmosphere.

Grading is carried out 6 to 7 days after the contamination, in comparison with the control plants. Under these conditions, good protection (at least 70%) is observed at a dose of 500 ppm with the following compounds: 2, 3, 4, 5, 7, 11, 12, 13, 17, 19, 25, 28, 31, 39, 40, 41, 42, 43, 44, 45, 47, 48, 51, 52, 53, 56, 65, 76, 79, 81, 82, 83, 85, 90, 92, 122, 138, 141 and 153.

Example E

In Vivo Test on *Botrytis cinerea* (Grey Mould)

The active ingredients tested are prepared by homogenization in a mixture of acetone/tween/DMSO, then diluted with water to obtain the desired active material.

Gherkin plants (Vert petit de Paris variety), sown on a 50/50 peat soil-pozzolana substrate in starter cups and grown at 18-20° C., are treated at the cotyledon Z11 stage by spraying with the active ingredient prepared as described above.

Plants, used as controls, are treated with an aqueous solution not containing the active material. After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:

20 g/L of gelatin;
50 g/L of D-fructose;
2 g/L of NH$_4$NO$_3$;
1 g/L of KH$_2$PO$_4$.

The contaminated cucumber plants are settled for 5-7 days in a climatic room at 15-11° C. (day/night) and at 80% relative humidity.

Grading is carried out 5/7 days after the contamination, in comparison with the control plants.

Under these conditions, good (at least 70%) protection is observed at a dose of 500 ppm with the following compounds: 1, 2, 5, 6, 12, 15, 16, 39, 40, 42, 44, 45, 51, 74, 76, 78, 85, 133 and 138.

Example F

In Vivo Test on *Sphaerotheca fuliginea* (Powdery Mildew)

The active ingredients tested are prepared by homogenization in a mixture of acetone/tween/water. This suspension is then diluted with water to obtain the desired active material concentration.

Gherkin plants (Vert petit de Paris variety) in starter cups, sown on a 50/50 peat soil-pozzolana substrate and grown at 20° C./23° C., are treated at the cotyledon Z10 stage by spraying with the aqueous suspension described above. Plants, used as controls, are treated with an aqueous solution not containing the active material.

After 24 hours, the plants are contaminated by spraying them with an aqueous suspension of *Sphaerotheca fuliginea* spores (100 000 spores per ml). The spores are collected from a contaminated plants. The contaminated gherkin plants are incubated at about 20° C./25° C. and at 60/70% relative humidity.

Grading (% of efficacy) is carried out 12 days after the contamination, in comparison with the control plants.

Under these conditions, good (at least 70%) or total protection is observed at a dose of 500 ppm with the following compounds: 1, 2, 3, 5, 6, 7, 8, 12, 13, 15, 16, 17, 22, 24, 30, 39, 40, 41, 42, 43, 44, 45, 46, 48, 49, 50, 51, 52, 54, 56, 57, 59, 62, 64, 65, 66, 67, 70, 71, 72, 73, 74, 75, 76, 78, 80, 84, 85, 87, 92, 95, 96, 104, 106, 115, 117, 122, 123, 125, 130, 131, 133, 134, 135, 136, 138, 146 and 147.

Example G

In Vivo Test on *Phakopsora pachyrhizi* (Soybean Rust)

The active ingredients tested are prepared by homogenization in a mixture of acetone/Emulgator PS16. This suspension is then diluted with water to obtain the desired active material concentration.

Soybean plants (Miyagishirome variety), sown on a horticultural soil in plastic pots and grown at 20° C., are treated at the 1.5-leaf stage (20 cm tall) by spraying with the aqueous suspension described above. Plants, used as controls, are treated with an aqueous solution not containing the active material.

After 24 hours, the plants are contaminated by spraying them with an aqueous suspension of *Phakopsora pachyrhizi* spores (100,000 spores per ml). The spores are collected from contaminated plants. The contaminated soybean plants are incubated at about 20° C. and at 80% relative humidity.

Grading is carried out 11 days after the contamination, in comparison with the control plants. Under these conditions, good (at least 70%) or total protection is observed at a dose of 250 ppm with the following compounds: 1, 12, 13, 17, 19, 31, 90 and 92.

The invention claimed is:
1. A compound of formula:

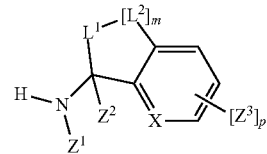

wherein
Z$^1$ is selected from the group consisting of a nonsubstituted C$_3$-C$_7$-cycloalkyl and a C$_3$-C$_7$-cycloalkyl which is substituted by up to 10 atoms or groups, wherein the substituent atoms or groups are independently selected from the group consisting of halogen atoms; cyano; C$_1$-C$_8$-alkyl; C$_1$-C$_8$-halogenoalkyl comprising up to 9 halogen atoms that can be the same or different; C$_1$-C$_8$-alkoxy; C$_1$-C$_8$-halogenoalkoxy comprising up to 9 halogen atoms that can be the same or different; C$_1$-C$_8$-alkoxycarbonyl; C$_1$-C$_8$-halogenoalkoxycarbonyl comprising up to 9 halogen atoms that can be the same or different; C$_1$-C$_8$-alkylaminocarbonyl; di-C$_1$-C$_8$-alkylaminocarbonyl; and carbamoyl;

$Z^2$ is selected from the group consisting of a hydrogen atom; a halogen atom; cyano; $C_1$-$C_8$-alkyl; and $C_1$-$C_8$-halogenoalkyl comprising up to 9 halogen atoms that can be the same or different;

$L^1$ and $L^2$ are independently selected from the group consisting of $CZ^4Z^5$;

m is 1 or 2;

X is $CZ^7$;

$Z^7$ and each $Z^3$ are independently selected from the group consisting of a hydrogen atom; a halogen atom; nitro; cyano; hydroxyl; thio; amino; pentafluoro-$\lambda^6$-thio; $C_1$-$C_4$-alkyl; $C_1$-$C_4$-halogenoalkyl comprising up to 9 halogen atoms that can be the same or different; $C_1$-$C_4$-alkylamino; di-$C_1$-$C_4$-alkylamino; $C_1$-$C_4$-alkoxy; $C_1$-$C_4$-halogenoalkoxy comprising up to 9 halogen atoms that can be the same or different; $C_1$-$C_4$-alkoxy-$C_1$-$C_4$-alkyl; $C_1$-$C_4$-alkylsulfanyl; $C_1$-$C_4$-halogenoalkylsulfanyl comprising up to 9 halogen atoms that can be the same or different; $C_2$-$C_4$-alkenyl; $C_2$-$C_4$-halogenoalkenyl comprising up to 9 halogen atoms that can be the same or different; $C_2$-$C_4$-alkynyl; $C_2$-$C_4$-halogenoalkynyl comprising up to 9 halogen atoms that can be the same or different; $C_2$-$C_4$-alkenyloxy; $C_2$-$C_4$-halogenoalkenyloxy comprising up to 9 halogen atoms that can be the same or different; $C_2$-$C_4$-alkynyloxy; $C_2$-$C_4$-halogenoalkynyloxy comprising up to 9 halogen atoms that can be the same or different; $C_3$-$C_7$-cycloalkyl; $C_3$-$C_7$-cycloalkyl-$C_1$-$C_4$-alkyl; $C_3$-$C_7$-halogenocycloalkyl comprising up to 9 halogen atoms that can be the same or different; formyl; formyloxy; formylamino; carboxy; carbamoyl; N-hydroxycarbamoyl; carbamate; (hydroxyimino)-$C_1$-$C_4$-alkyl; $C_1$-$C_4$-alkylcarbonyl; $C_1$-$C_4$-halogenoalkylcarbonyl comprising up to 9 halogen atoms that can be the same or different; $C_1$-$C_4$-alkylcarbamoyl; di-$C_1$-$C_4$-alkylcarbamoyl; —$C_1$-$C_4$-alkyloxycarbamoyl; $C_1$-$C_4$-alkoxycarbamoyl; —$C_1$-$C_4$-alkyl-$C_1$-$C_4$-alkoxycarbamoyl; $C_1$-$C_4$-alkoxycarbonyl; $C_1$-$C_4$-halogenoalkoxycarbonyl comprising up to 9 halogen atoms that can be the same or different; $C_1$-$C_4$-alkylaminocarbonyl; di-$C_1$-$C_4$-alkylaminocarbonyl; $C_1$-$C_4$-alkylcarbonyloxy; $C_1$-$C_4$-halogenoalkylcarbonyloxy comprising up to 9 halogen atoms that can be the same or different; $C_1$-$C_4$-alkylcarbonylamino; $C_1$-$C_4$-halogenoalkylcarbonylamino comprising up to 9 halogen atoms that can be the same or different; $C_1$-$C_4$-alkylaminocarbonyloxy; di-$C_1$-$C_4$-alkylaminocarbonyloxy; $C_1$-$C_4$-alkyloxycarbonyloxy; $C_1$-$C_4$-alkylsulfenyl; $C_1$-$C_4$-halogenoalkylsulfenyl comprising up to 9 halogen atoms that can be the same or different; $C_1$-$C_4$-alkylsulfinyl; $C_1$-$C_4$-halogenoalkylsulfinyl comprising up to 9 halogen atoms that can be the same or different; $C_1$-$C_4$-alkylsulfonyl; $C_1$-$C_4$-halogenoalkylsulfonyl comprising up to 9 halogen atoms that can be the same or different; $C_1$-$C_4$-alkoxyimino; ($C_1$-$C_4$-alkoxyimino)-$C_1$-$C_4$-alkyl; ($C_1$-$C_4$-alkenyloxyimino)-$C_1$-$C_4$-alkyl; ($C_1$-$C_4$-alkynyloxyimino)-$C_1$-$C_4$-alkyl; (benzyloxyimino)-$C_1$-$C_4$-alkyl; phenyl that can be substituted by up to two groups Q; benzyloxy that can be substituted by up to two groups Q; benzylthio that can be substituted by up to two groups Q; benzylamino that can be substituted by up to two groups Q; naphthyl that can be substituted by up to two groups Q; phenoxy that can be substituted by up to two groups Q; phenylamino that can be substituted by up to two groups Q; phenylthio that can be substituted by up to two groups Q; phenylmethylene that can be substituted by up to two groups Q; pyridinyl that can be substituted by up to two groups Q; pyridinyloxy that can be substituted by up to two groups Q; and phenoxymethylene that can be substituted by up to two groups Q; or two substituents $Z^3$ or $Z^7$ together with the consecutive carbon atoms to which they are linked can form a 5- or 6-membered, saturated or non-saturated, carbo- or hetero-cycle, that can be substituted by up to two groups Q that can be the same or different;

p is 1 or 2;

$Z^4$ and $Z^5$ are independently selected from the group consisting of a hydrogen atom; a halogen atom; cyano; nitro; $C_1$-$C_8$-alkyl; $C_1$-$C_8$-halogenoalkyl comprising up to 9 halogen atoms that can be the same or different; $C_1$-$C_8$-alkoxy; $C_1$-$C_8$-halogenoalkoxy comprising up to 9 halogen atoms that can be the same or different; $C_1$-$C_8$-alkoxy-$C_1$-$C_8$-alkyl; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; $C_1$-$C_8$-alkylcarbonyl; $C_1$-$C_8$-halogenoalkylcarbonyl comprising up to 9 halogen atoms that can be the same or different; $C_1$-$C_8$-alkylsulfanyl; $C_1$-$C_8$-halogenoalkylsulfanyl comprising up to 9 halogen atoms that can be the same or different; $C_1$-$C_8$-alkylsulfinyl; $C_1$-$C_8$-halogenoalkylsulfinyl comprising up to 9 halogen atoms that can be the same or different; $C_1$-$C_8$-alkylsulfonyl; and $C_1$-$C_8$-halogenoalkylsulfonyl comprising up to 9 halogen atoms that can be the same or different;

each Q is independently selected from the group consisting of a halogen atom; cyano; nitro; $C_1$-$C_4$-alkyl; $C_1$-$C_4$-halogenoalkyl comprising up to 9 halogen atoms that can be the same or different; $C_1$-$C_4$-alkoxy; $C_1$-$C_4$-halogenoalkoxy comprising up to 9 halogen atoms that can be the same or different; $C_1$-$C_4$-alkylsulfanyl; and $C_1$-$C_4$-halogenoalkylsulfanyl comprising up to 9 halogen atoms that can be the same or different;

provided that:

(A) $Z^4$ and $Z^5$ cannot all be hydrogen; and (B) the compound is not 3-(cyclopropylamino)-2,3-dihydro-1,7-dimethyl-1H-indan-4-ol.

2. The compound of claim 1 wherein $Z^1$ is a cyclopropyl.

3. The compound of claim 1 wherein $Z^1$ is a non-substituted cyclopropyl.

4. The compound of claim 1 wherein $Z^2$ is a hydrogen atom.

5. The compound of claim 1 wherein $Z^7$ and each $Z^3$ are independently selected from the group consisting of a hydrogen atom; a halogen atom; $C_1$-$C_4$-alkyl; $C_1$-$C_4$-halogenoalkyl comprising up to 9 halogen atoms that can be the same or different; $C_1$-$C_4$-alkoxy; and $C_1$-$C_4$-halogenoalkoxy comprising up to 9 halogen atoms that can be the same or different.

* * * * *